US007790735B2

(12) United States Patent
Jacobson et al.

(10) Patent No.: US 7,790,735 B2
(45) Date of Patent: Sep. 7, 2010

(54) METHANOCARBA CYCLOALKYL NUCLEOSIDE ANALOGUES

(75) Inventors: Kenneth A Jacobson, Silver Spring, MD (US); Victor E Marquez, Montgomery Village, MD (US)

(73) Assignee: The United States of America as represented by the Department of Health and Human Services, Bethesda, MD (US)

( * ) Notice: Subject to any disclaimer, the term of this patent is extended or adjusted under 35 U.S.C. 154(b) by 111 days.

(21) Appl. No.: 11/500,860

(22) Filed: Aug. 8, 2006

(65) Prior Publication Data

US 2006/0270629 A1 Nov. 30, 2006

Related U.S. Application Data

(62) Division of application No. 10/169,975, filed as application No. PCT/US01/00981 on Jan. 12, 2001, now Pat. No. 7,087,589.

(60) Provisional application No. 60/176,373, filed on Jan. 14, 2000.

(51) Int. Cl.
*C07D 239/54* (2006.01)
*A61K 31/513* (2006.01)
(52) U.S. Cl. ..................... 514/269; 544/309
(58) Field of Classification Search ............... 544/309; 514/269
See application file for complete search history.

(56) References Cited

U.S. PATENT DOCUMENTS

| 2,577,706 | A | 12/1951 | Hotten |
| 3,146,211 | A | 8/1964 | Errede |
| 3,984,406 | A | 10/1976 | Quadbeck-Seeger et al. |
| 4,048,171 | A | 9/1977 | Bossert et al. |
| 4,072,633 | A | 2/1978 | Hermans |
| 4,548,818 | A | 10/1985 | Kjellin et al. |
| 4,659,717 | A | 4/1987 | Wikel |
| 4,672,068 | A | 6/1987 | Kutsuma et al. |
| 4,772,607 | A | 9/1988 | Badger et al. |
| 4,866,072 | A | 9/1989 | Edwards et al. |
| 4,954,504 | A | 9/1990 | Chen et al. |
| 5,032,593 | A | 7/1991 | Rzeszotarski et al. |
| 5,063,233 | A | 11/1991 | Chen et al. |
| 5,096,916 | A | 3/1992 | Skupin |
| 5,140,015 | A | 8/1992 | Olsson et al. |
| 5,284,834 | A | 2/1994 | Jacobson et al. |
| 5,310,731 | A | 5/1994 | Olsson et al. |
| 5,366,977 | A | 11/1994 | Pollard et al. |
| 5,443,836 | A | 8/1995 | Downey et al. |
| 5,498,605 | A | 3/1996 | Jacobson et al. |
| 5,620,676 | A | 4/1997 | Jacobson et al. |
| 5,629,454 | A | 5/1997 | Marquez et al. |
| 5,688,774 | A | 11/1997 | Jacobson et al. |
| 5,773,423 | A | 6/1998 | Jacobson et al. |
| 5,840,728 | A | 11/1998 | Marquez et al. |
| 5,877,179 | A | 3/1999 | Pollard et al. |
| 6,066,642 | A | 5/2000 | Jacobson et al. |
| 7,009,050 | B2* | 3/2006 | Marquez et al. ............ 544/309 |
| 2004/0142946 | A1 | 7/2004 | Chattopadhyaya |

FOREIGN PATENT DOCUMENTS

| DE | 4325254 A1 | 2/1994 |
| EP | 0 374 808 A2 | 6/1990 |
| EP | 0 577 558 A2 | 1/1994 |
| EP | 0 217 530 | 4/1997 |
| WO | WO 94/03456 A1 | 2/1994 |
| WO | WO 94/25605 A1 | 11/1994 |
| WO | WO 94/25607 A1 | 11/1994 |
| WO | WO 95/03304 A1 | 2/1995 |
| WO | WO 95/08541 A1 | 3/1995 |
| WO | WO 96/02553 A2 | 2/1996 |
| WO | WO 96/16084 A2 | 5/1996 |
| WO | WO 97/27177 A2 | 7/1997 |
| WO | WO 98/05662 A1 | 2/1998 |

OTHER PUBLICATIONS

Feoktistov et al., Adenosine A2B receptors, Pharmacological Reviews, vol. 49, No. 4, pp. 381-402, 1997.*
Baraldi et al., Pyrazolo-triazolo-pyrimidine derivatives as adenosine receptor antagonists: a possible template for adenosine receptor subtypes?, Current Pharmaceutical Design, vol. 8, No. 26, pp. 2299-2332, 2002.*
Chao et al., Synthsis of Bicarbocyclic Dideoxynucleosides as Potential Antiviral Agesnts, Tetrahedron, vol. 53, No. 6, pp. 1957-1970, 1997.*
Simone, Oncology: Introduction, Cecil Textbook of Medicine, 20th Edition, vol. 1, pp. 1004-1010, 1996.*
Damasio, Alzheimer's Disease and related dementias, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*
Ali et al., *JPET-Abstracts*, 276(2), 837-845 (1996).
Altmann et al., *Tetrahedron Letters*, 35(15), 2331-2334 (1994).
Altmann et al., *Tetrahedron Letters*, 35(41), 7625-7628 (1994).
Alzheimer et al., *Neuroscience Letters*, 99(1,2), 107-112 (1989).
Beach et al., *American Journal of Physiology*, 263(3), 3pages, including abstract (1992).
Bowler et al., *Drug Devel. Res.*, 43, 26 (1998).

(Continued)

*Primary Examiner*—Deepak Rao
(74) *Attorney, Agent, or Firm*—Leydig, Voit & Mayer, Ltd.

(57) ABSTRACT

The present invention provides novel nucleoside and nucleotide derivatives that are useful agonist or antagonists of P1 and P2 receptors. For example, the present invention provides a compound of formula A-M, wherein A is modified adenine or uracil and M is a constrained cycloalkyl group. The adenine or uracil is bonded to the constrained cycloalkyl group. The compounds of the present invention are useful in the treatment or prevention of various diseases including airway diseases (through $A_{2B}$, $A_3$, $P2Y_2$ receptors), cancer (through $A_3$, P2 receptors), cardiac arrhythmias (through A1 receptors), cardiac ischemia (through $A_1$, $A_3$ receptors), epilepsy (through $A_1$, P2X receptors), and Huntington's Disease (through $A_{2A}$ receptors).

17 Claims, No Drawings

OTHER PUBLICATIONS

Brackett et al., *Biochemical Pharmacology*, 39(12), 1897-1904 (1990).
Bruns et al., *Proc. Natl. Acad. Sci.*, 77(9), 5547-5551 (1980).
Bruns et al., *Molecular Pharmacology*, 2, 331-346 (1986).
Bruns et al., *Nucleosides & Nucleotides*, 10(5), 931-943 (1991).
Carruthers et al., *Reprinted from Trends in Pharmacological Sciences*, 14(8), 290-291 (1993).
Daly, *Caffeine, Coffee, and Health*, edited by S. Garatini, Published by Raven Press, Ltd., New York, 97-150 (1993).
De et al., *Society for Neuroscience Abstracts*, 19 (1993).
Dyatkina et al., *Bioorganic & Medicinal Letters*, 6(22), 2639-2642 (1996).
Eidelman et al., *Proc. Natl. Acad. Sci.*, 89, 5562-5566, (1992).
Ezzitouni et al., *J. Chem. Soc., Chem. Commun.*, 1345-1346 (1995).
Ezzitouni et al., *J. Chem. Soc., Perkin Trans. 1*, 1073-1078 (1997).
Ezzitouni et al., *J. Org. Chem.*, 62, 4870-4873 (1997).
Fischer et al., *Drug Devel. Res.*, 43, 28 (1998).
Fozard et al., *Br. J. Pharmacol.*, 109, 3-5 (1993).
Gong, *Heteroatom Chemistry*, 14(1), 13-17 (2003).
Hackh's Chemical Dictionary, $5^{th}$ edition, p. 444 (1987).
Jacobson et al., "Novel Selective Non-Xanthine $A_3$ Adenosine Receptor Antagonists", *Abstract from Purines*, (1996).
Jacobson et al., *Biochemistry*, 34, 9088-9094 (1995).
Jacobson et al., *FEBS Letters*, 323(1,2), 141-144 (1993).
Jacobson et al., *Journal of Medicinal Chemistry*, 35(22), 4143-4149 (1992).
Jacobson et al., *Journal of Medicinal Chemistry*, 35(3), 407-422 (1992).
Jacobson et al., *Purinergic Approaches in Experimental Therapeutics*, Chapter 6, 101-128 (1997).
Jacobson et al., *The P2 Nucleotide Receptors, Eds.*, Chap. 4, 81-107.
Jacobson, "Adenosine ($P_1$) and ATP ($P_2$) Receptors" 12.10, 601-642.
Jeong et al., *Nucleosides & Nucleotides*, 16(7-9), 1059-1062 (1997).
Jeong et al., *Tetrahedron Letters*, 37(14), 2353-2356 (1996).
Ji et al., "Flavonoid Derivatives as $A_3$ Adenosine Receptor Antagonists", *Abstract from Purines*, (1996).
Ji et al., *Biochem. Biophys. Res. Comm.*, 203(1), 570-576 (1994).
Ji et al., *Drug Development Research*, 33:00-00, 11 pages (1994).
Jiang et al., *J. Med. Chem.*, 39, 4667-4675 (1996).
Jiang et al., *Med. Chem.*, 40, 2596-2608 (1997).
Karton et al., *J. Med. Chem.*, 39, 2293-2301 (1996).
Katagiri et al., *Tetrahedron Letters*, 40, 9069-9072 (1999).
Kim et al., *J. Med. Chem.*, 39, 4141-4148 (1996).
Kim et al., *Journal of Medicinal Chemistry*, 45(1), 208-218 (2002).
Knoblauch et al., *Drug Devel. Res.*, 43, 34 (1998).
Knutsen et al., *Drug Devel. Res.*, 43, 25 (1998).
Kononova, *Biochemistry* (Moscow), 67(2), 184-195 (2002).
Li et al., *J. Med. Chem.*, 41, 3186-3201 (1998).
Lopin, *J. Org. Chem.*, 68(26), 9916-9923 (2003).
Marquez et al., *Helvetica Chimica Acta*, 82, 2119-2139 (1999).
Marquez et al., *J. Am. Chem. Soc.*, 120, 2780-2789 (1998).
Marquez et al., *J. Med. Chem.*, 39, 3739-3747 (1996).
Marquez et al., *Nucleosides & Nucleotides*, 16(7-9), 1431-1434 (1997).
Marquez et al., *Nucleosides & Nucleotides*, 18(4 & 5), 521-530 (1999).
Miriam Webster Online Dictionary definition for phosphoryl <http://www.m-w.com/cgi-bin/dictionary?book=Dictionary&va=phosphoryl> downloaded from the Internet Feb. 23, 2004.
Moon et al., *J. Org. Chem.*, 64, 4733-4741 (1999).
Online Source "phosphoric acids" http://www.chemsoc.org/chembytes/goldbook/P04560.PDF downloaded from the Internet May 31, 2005.
Ramkumar et al., *J. Biol. Chem.*, 268(23), 16887-16889 (1993).
Ravi et al., *Drug Development Research*, 53, 1-12 (2001).
Registry File for RN 129687-40-7.
Registry File for RN 146038-94-0.
Registry File for RN 159967-50-7.
Rodriguez et al., *J. Med. Chem.*, 37, 3389-3399 (1994).
Rodriguez et al., *Tetrahedron Letters*, 34(39), 6233-6236 (1993).
Ruan, *Journal of Applied Polymer Science*, 92(3), 1618-1624 (2004).
Shin et al., *J. Org. Chem.*, 65, 2172-2178 (2000).
Shuto et al., *J. Org. Chem.*, 63, 1986-1994 (1998).
Siddiqui et al., *Nucleosides & Nucleotides*, 15(1-3), 235-250 (1996).
Sluggett, *J. Amer. Chem. Soc.*, 117, 5148-5153 (1995).
Snowdy et al., *Drug Devel. Res.*, 43, 30 (1998).
Spalluto et al., *Drug Devel. Res.*, 43, 30 (1998).
Sumiyoshi, *Die Makromolekulare Chemie*, 186(9), 1811-1823 (1985).
Theil et al., *J. Chem. Soc., Perkin Trans. 1*, 255-258 (1996).
Turro, *Chemical Physics Letter*, 193, 546 (1992).
Van Bergen et al., *Abstract of American Chemical Society Meeting*, Chicago, Illinois (Aug. 25, 1993).
Van Galen et al., *Cleosides & Nucleotides*, 10(5), 1191-1193 (1991).
Van Rhee et al., "Development of 1,4-Dyhydropyridines as Selective $A_3$ Adenosine Receptor Antagonists" *Abstract from Purines*, (1996).
Van Rhee et al., *J. Med. Chem.*, 39, 2980-2989 (1996).
Volpini et al., "Potent and Selective Adenotin Agonists: 2' and 3'-Deoxy Derivatives of 5'-N-Methylcarboxamidoadenosine (MECA)", *Abstract from Purines*, (1996).
Von Lubitz et al., *European Journal of Pharmacology*, 263, 59-67 (1994).
Von Lubitz et al., *European Journal of Pharmacology*, 54886, 1-6 (1996).
Ward et al., $48^{th}$ *Annual Meeting—Society of General Physiologist*, Abstract 33a.
Williams et al., *Drug Development Research*, 43(1), 5 pages (25, 26, 28, 30, 34), (1998).
Zhou et al., *Proc. Natl. Acad. Sci.*, 89, 7432-7436 (1992).

\* cited by examiner

METHANOCARBA CYCLOALKYL NUCLEOSIDE ANALOGUES

CROSS-REFERENCE TO RELATED APPLICATIONS

This is a divisional of co-pending U.S. patent application Ser. No. 10/169,975, which is the U.S. national stage of PCT/US01/00981, filed Jan. 12, 2001, claiming the benefit of U.S. Provisional Patent application No. 60/176,373, filed Jan. 14, 2000, the disclosures of which are incorporated by reference.

TECHNICAL FIELD OF THE INVENTION

This invention pertains to a novel class of receptor ligands for P1 and P2 receptors and their therapeutic use. More specifically, the invention pertains to nucleoside derivatives in which the sugar moiety is replaced with a cycloalkyl group that is conformationally constrained by fusion to a second cycloalkyl group.

BACKGROUND OF THE INVENTION

Purines such as adenosine have been shown to play a wide array of roles in biological systems. For example, physiological roles played by adenosine include, inter alia, modulator of vasodilation and hypotension, muscle relaxant, central depressant, inhibitor of platelet aggregation, regulator of energy supply/demand, responder to oxygen availability, neurotransmitter, and neuromodulator. (Bruns, Nucleosides & Nucleotides, 10(5), 931-934 (1991)). Because of its potent actions on many organs and systems, adenosine and its receptors have been the subject of considerable drug-development research (Daly, J. Med. Chem., 25, 197 (1982)). Potential therapeutic applications for agonists include, for instance, the prevention of reperfusion injury after cardiac ischemia or stroke, and treatment of hypertension and epilepsy (Jacobson, et al., J. Med. Chem., 35, 407-422 (1992)). Adenosine itself has recently been approved for the treatment of paroxysmal supra ventricular tachycardia (Pantely, et al., Circulation, 82, 1854 (1990)). Adenosine receptor agonists also find use as anti-arrhythmics, antinociceptives, anti-lipolytics, cerebroprotectives, and antipsychotics.

P2 receptors, are present in heart, skeletal, various smooth muscles, prostate, ovary, and brain and have been implicated in certain aggregation processes associated with thrombosis and as anti-hypertensive and anti-diabetic agents. Agonists that bind the P2 receptor induce activation of phospholipase C, which leads to the generation of inositol phosphates and diacyl glycerol with a subsequent rise in intracellular calcium concentration and muscle relaxation. P2 receptor antagonists block ADP-promoted aggregation in platelets and thereby exert an anti-thrombotic effect.

All P1 and P2 receptor nucleoside ligands suffer from chemical instability that is caused by the labile glycosidic linkage in the sugar moiety of the nucleoside. However, it has been found that relatively few ribose modifications are tolerated by the presently known agonists and antagonists of P1 and P2 receptors.

New compositions are needed that have improved chemical stability and that do not destroy the activity of such compounds.

The invention provides such compositions and methods of using them in the treatment of disease. These and other advantages of the present invention, as well as additional inventive features, will be apparent from the description of the invention provided herein.

BRIEF SUMMARY OF THE INVENTION

The present invention provides novel nucleoside and nucleotide derivatives that are useful agonists or antagonists of P1 or P2 receptors. The invention is premised upon the novel combination of adenine and uracil and their derivatives with a constrained cycloalkyl group, typically a cyclopentyl group. The constraint on the cycloalkyl group is introduced by fusion to a second cycloalkyl group. In the case of cyclopentane, the fusion is typically with cyclopropane. The present compounds retain a surprising binding affinity despite the substitution for the ribose group. Moreover, the absence of the glycosidic bond in the compounds assists in improving the chemical stability of the compounds and aids in overcoming the stabilit problem associated with the glycosidic bond in previously known P1 and P2 receptor ligands.

The compounds of the present invention are useful in the treatment or prevention of various airway diseases (through $A_{2B}$, $A_3$, $P2Y_2$ receptors), cancer (through $A_3$, P2 receptors), cardiac arrhythmias (through $A_1$ receptors), cardiac ischemia (through $A_1$, $A_3$ receptors), epilepsy (through $A_1$, P2X receptors), Huntington's Disease (through $A_{2A}$ receptors), Immunodeficient disorders (through $A_2$, $A_3$ receptors), inflammatory disorders (through $A_3$, $P_2$ receptors), neonatal hypoxia (through $A_1$ receptors), neurodegenerative (through $A_1$, $A_3$, P2 receptors), pain (through $A_1$, $A_3$, P2X3 receptors), Parkinson's Disease (through $A_{2A}$ receptors), renal failure (through $A_1$ receptors), schizophrenia (through $A_{2A}$ receptors), sleep disorders (through $A_1$ receptors), stroke (through $A_1$, $A_3$, P2 receptors), thrombosis (through $P2Y_1$, $P2Y_{AC}$ receptors), urinary incontinence (through $P2X_1$ receptors), diabetes (through $A_1$ receptors), psoriasis (through P2X receptors), septic shock (through P2 receptors), brain trauma (through $A_1$ receptors), glaucoma (through $A_3$ receptors) and congestive heart failure (through P2 receptors).

The invention may best be understood with reference to the accompanying drawings and in the following detailed description of the preferred embodiments.

DETAILED DESCRIPTION OF THE INVENTION

The present invention provides a new class of nucleoside and nucleotide analogs that serve as selective agonists or antagonists for P1 and P2 receptors.

Generally, the compounds of the present invention comprise two basic chemical components designated "A" and "M" which are covalently bonded to one another. Component A comprises adenine or uracil, and component M includes a constrained cycloalkyl group. Preferably the adenine and uracil are chemically modified or substituted with moieties that allow the compound to bind to a P1 or P2 receptor. To that end any of a wide variety of chemical groups can be used to modify adenine and uracil. Those groups are well known to those of skill in the receptor art. Preferably, when A is purine or a purine derivative, the linkage between A and M is a chemical bond between the N9 purine nitrogen and the C1 carbon of the cycloalkyl group. Where A is pyrimidine or a pyrimidine derivative, the bond is between N1 pyrimidine nitrogen and the C1 carbon of the cycloalkyl group. The compounds of the present invention have improved stability and surprising receptor binding affinity.

While not wishing to be bound to any particular theory, it is believed that the constrained cycloalkyl group assists in improving chemical stability and receptor affinity. Preferably the cycloalkyl groups are capable of adopting a conformation such that the compound can bind to P1 or P2 receptors. As a result, preferred cycloalkyl groups are those that tend to form energetically favorable interactions with P1 and P2 receptors and avoid energetically unfavorable ones, such as unfavorable ionic and/or steric interactions. Further, the cycloalkyl group is derivatized with a bridging group. The constraint restricts the cycloalkyl group to certain conformations that are believed to be beneficial to binding affinity. The preferred cycloalkyl group is a cyclopentyl group. With cyclopentyl groups the preferred method for introducing a conformational constraint is by derivatizing with a fused cyclopropane bridge. With this modification the cyclopentane ring is believed to be constrained to mimic the conformation of a rigid furanose ring.

Compounds of the present invention include the compounds shown below in Formulae I and II.

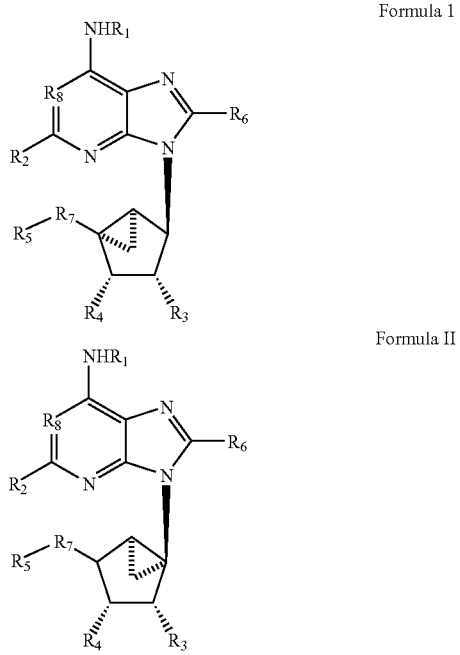

Formulae I and II show compounds in which a derivatized or underivatized adenine base is joined to a constrained cyclopentyl group. For purposes of reference, the carbon atom of the cyclopentyl group, M, that is joined to adenine, A, is the C1 carbon and the adenine is joined to M through its N9 nitrogen. In the compounds of Formulae I and II the constrained cyclopentyl group is derivatized with a fused cyclopropane bridge. In Formula I the cyclopropyl group bridges carbon atoms C4 and C6. In Formula II the cyclopropyl group bridges carbon atoms C6 and C1. These distinct bridging patterns constrain the cyclopentyl group into distinct conformations, specifically the N-(northern) conformation as in Formula I and the S-(southern) conformation as in Formula II. These two conformations are thought to mimic the two biologically active conformations of furanose groups for P1 and P2 receptor binding pockets.

The compounds described by Formulae I and II can be further defined by a variety of suitable modifications to the adenine group. As discussed above, any of a wide variety of chemical groups can be used to form suitable adenine derivatives that comprise the novel compounds of the present invention, provided that the resulting compound is capable of binding to a P1 or P2 receptor. These chemical groups are well known in the art and have been described, for example in U.S. Pat. Nos. 5,284,834; 5,498,605; 5,620,676; 5,688,774; and Jacobson and Van Rhee, PURINERGIC APPROACHES IN EXPERIMEN- TAL THERAPEUTICS, Chapter 6, p. 101 (Jacobson and Jarvis eds., 1997); and Jacobson et al., THE P2 NUCLEOTIDE RECEPTORS, p. 81-107, in THE RECEPTORS (Turner et al. eds. 1998), which are incorporated by reference herein. The combination of the chemically modified adenine and the constrained cycloalkyl group provides a surprising improvement in both chemical stability and binding affinity.

By way of example and not in limitation of the present invention in the compounds of Formulae I and II, $R_1$ is hydrogen, alkyl, cycloalkyl, alkoxy, cycloalkoxy, aryl, arylalkyl, acyl, sulfonyl, arylsulfonyl, thiazolyl or bicyclic alkyl; $R_2$ is hydrogen, halo, alkyl, aryl, arylamino, aryloxide, alkynyl, alkenyl, thioether, cyano, alkylthio or arylalkylthio; $R_3$, $R_4$, and $R_5$, are each hydrogen, hydroxyl, alkoxy, alkyl, alkenyl, alkynyl, aryl, acyl, alkylamino, arylamino, phosphoryl, phosphonyl, boronyl, or vanadyl, and they can be the same or different; $R_6$ is hydrogen, alkyl, alkenyl, alkynyl, or aminoalkyl. $R_7$ is a methylene, dihalomethyl, carbonyl, or sulfoxide group. $R_8$ is carbon or nitrogen. At least one of $R_1$, $R_2$, and $R_6$ is not hydrogen. It can be appreciated that various combinations of the above groups are also within the invention provided that they retain agonist or antagonist activity with a P1 or P2 type receptor.

Where an alkyl, alkenyl, alkynyl group is referenced by itself or as part of another group, the reference is to an uninterrupted carbon chain consisting of no more than 20 carbon atoms. Aryl and cycloalkyl groups contain no more than 8 carbons in the ring.

Reference to alkyl groups is further meant to include straight or branched chain alkyls, arylalkyl, aminoalkyl, haloalkyl, alkylthio or arylalkylthio groups. Alkyls specifically include methyl through dodecyl. Where alkyl groups are present at position $R_6$ in adenine, it is preferred that the chain length be no longer than 6 carbons. Arylalkyl groups include, phenylisopropyl, phenylethyl. Aminoalkyl groups can be any suitable alkyl group also containing an amine. Similarly, haloalkyl groups can be any suitable alkyl group that contains a halo substituent, such as bromo, chloro, flouro, iodo. Alkylthio includes such moieties as thiomethyl, thiopentyl, thiohexyl, thioheptyl, thiooctyl, thiodecyl, thioundecyl, ethylthioethyl, or 6-cyanohexylthio groups. Alkylthio also is meant to include arylalkylthio such as 2-(p-nitrophenyl)ethyl)thio, 2-aminophenylethylthio, 2-(p-nitrophenyl)ethylthio, or 2-aminophenylethylthio.

Cycloalkyls for example cyclopentyl, cyclohexyl, hydroxycyclopentyl.

Alkoxys include for example methoxy groups.

Cycloalkoxys can include cyclopentoxy.

Aryl moieties can be arylalkyl, arylalkylthio, arylsulfonyl, arylamino, aryloxide, heteroaryl, haloaryl, arylurea, arylcarboxamido, heteroarylamino or sulfoaryl. Benzyl groups are one species of aryl group. In addition, the arylalkyls include R-phenylisopropyl or phenylethyl. Aryloxides can be phenyl, R-phenylisopropyl, phenylethyl, 3,5-dimethoxyphenyl-2-(2-methylphenyl)ethyl and sulfophenyl. Haloaryl can be iodobenzyl among other halogenated aryl groups. Additionally, the heteroaryls include, for example, furans such as tetrahydrofuran.

Acyl groups include carbonyls.

Alkenyl groups are analogous to alkyl groups but include at least one carbon-carbon double bond. When present at the $R_6$ group of adenine it is preferred that the carbon chain length be from 2 to 6 carbons.

Similarly, alkynyls are analogous to alkenyl groups but contain at least one triple carbon-carbon bond. As with other groups, when present at the $R_6$ position of adenine it is preferred that they are not longer than 6 carbons.

Phosphoryl groups include diphosphoryl, triphosphoryl, thiophosphoryl, thiodiphosphoryl, thiotriphosphoryl, imidodiphosphate, imidotriphosphate, methylene diphosphate, methylenetriphosphate, halomethylene diphosphate, halomethylene triphosphate, boranophosphate, boranodiphosphate, boranotriphosphate, or phosphorothioate-2-thioether for example.

Thio groups include alkylthio, arylalkylthio, alkenylthio, or arylthios. Alkylthio includes such groups as thiomethyl, thiopentyl, thiohexyl, thioheptyl, thiooctyl, thiodecyl, thioundecyl, ethylthioethyl, or 6-cyanohexylthio. Alkenylthio includes 5-hexenylthio. Arylthios include 2-(p-nitrophenyl) ethyl)thio, 2-aminophenylethylthio, 2-(p-nitrophenyl)ethylthio, or 2-aminophenylethylthio.

One example of a suitable thiazolyl is (benzothiazolyl) thio-2-propyl.

Examples of bicycloalkyls include s-endonorbornyl, or carbamethylcyclopentane.

Halo groups include such elements as fluoro, bromo, chloro, or iodo.

It will also be appreciated that any group that may be further substituted can be, and still be within the scope of the invention. For example, all of the $R_1$ groups except hydrogen can be further substituted. By way of illustration, when $R_1$ is not hydrogen, it can be further modified by substitutions with any of the following chemical substituents including amino, cyano, alkoxyl, alkyl, alkenyl, alkynyl, cycloalkyl, aryl, arylalkyl, acyl, halo, hydroxy, phosphoryl, sulfonyl, sulfonamido, carboxyl, thiohydroxyl, sulfonamido, carboxyl, and carboxamido groups. Similarly, for $R_2$-$R_{10}$ all of the groups other than hydrogen can be substituted further. Multiple substitutions are also contemplated.

In a preferred embodiment $R_1$ can be either methyl, cyclopentyl, cyclohexyl, phenyl, R-phenylisopropyl, benzyl, or phenylethyl; $R_2$ is chloride; and $R_6$ can be a $C_1$-$C_6$ alkylamino, $C_1$-$C_6$ alkyl, $C_1$-$C_6$ alkenyl, $C_1$-$C_6$ alkynyl group.

Other compounds of the present invention include the compounds shown below in Formulae III and IV. The Formulae show compounds in which a derivatized or underivatized uracil base is joined to a constrained cyclopentyl group.

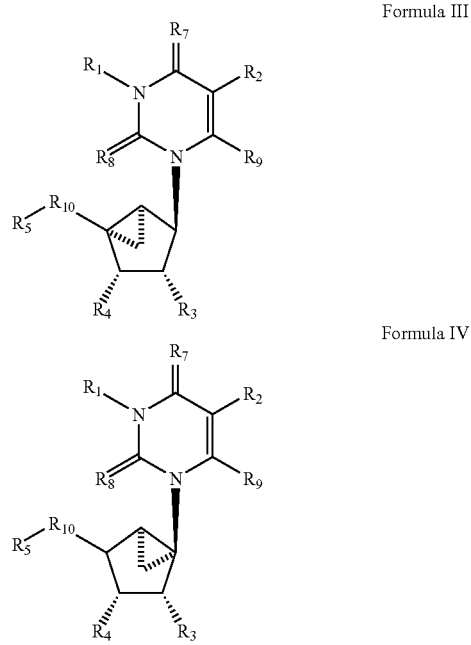

Formula III

Formula IV

The compounds defined by formulae III and IV can be further defined by a variety of suitable modifications. For example $R_1$ can be hydrogen, or an alkyl group; $R_2$ can be hydrogen, $C_1$-$C_6$ alkyl, $C_1$-$C_6$ alkenyl, $C_1$-$C_6$ alkynyl, or a $C_1$-$C_6$ aminoalkyl group; $R_3$, $R_4$, $R_5$, can each independently be the same as discussed previously with respect to Formulae 1 and Formulae II. $R_6$ and $R_7$ are each independently either sulfur or oxygen.

Certain compounds of the present invention are ligands of P2 receptors. A variety of P2 receptors are known in the art and the present compounds act at one or more of these, which include for example, P2X and P2Y receptors. These Receptor ligands are compounds that bind receptors, preferably in the binding pocket. In certain embodiments the compound can be a P2 receptor agonist. In other embodiments the compound can be a P2 receptor antagonist.

Certain compounds of the present invention are ligands for the P1 receptor. A variety of subclasses of P1 receptors are known and various of present compounds act at one or more these species, which include for example $A_1$, $A_2$, and $A_3$ receptors. Certain compounds act as P1 receptor agonists while others appear to act as antagonists.

The compounds of the present invention are useful in the treatment or prevention of various airway diseases (through $A_{2B}$, $A_3$, P2Y$_2$ receptors), cancer (through $A_3$, P2 receptors), cardiac arrhythmias (through $A_1$ receptors), cardiac ischemia (through $A_1$, $A_3$ receptors), epilepsy (through $A_1$, P2X receptors), Huntington's Disease (through $A_{2A}$ receptors), Immunodeficient disorders (through $A_2$, $A_3$ receptors), inflammatory disorders (through $A_3$, $P_2$ receptors), neonatal hypoxia (through $A_1$ receptors), neurodegenerative (through $A_1$, $A_3$, P2 receptors), pain (through $A_1$, $A_3$, P2X3 receptors), Parkinson's Disease (through $A_{2A}$ receptors), renal failure (through $A_1$ receptors), schizophrenia (through $A_{2A}$ receptors), sleep disorders (through $A_1$ receptors), stroke (through $A_1$, $A_3$, P2 receptors), thrombosis (through P2Y$_1$, P2Y$_{AC}$ receptors), urinary incontinence (through P2X$_1$ receptors), diabetes (through $A_1$ receptors), psoriasis (through P2X receptors), septic shock (through P2 receptors), brain trauma (through $A_1$ receptors), glaucoma (through $A_3$ receptors), and congestive heart failure (through P2 receptors).

The present invention is further directed to a pharmaceutical composition comprising a pharmaceutically acceptable carrier and at least one compound selected from the group consisting of the presently described compounds.

The pharmaceutically acceptable excipients described herein, for example, vehicles, adjuvants, carriers or diluents, are well-known to those who are skilled in the art and are readily available to the public. It is preferred that the pharmaceutically acceptable carrier be one that is chemically inert to the active compounds and one that has no detrimental side effects or toxicity under the conditions of use.

The choice of excipient will be determined in part by the particular compound of the present invention chosen, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular, interperitoneal, rectal, and vaginal administration are merely exemplary and are in no way limiting.

One skilled in the art will appreciate that suitable methods of utilizing a compound and administering it to a mammal for the treatment of disease states, which would be useful in the method of the present invention, are available. Although more than one route can be used to administer a particular compound, a particular route can provide a more immediate and more effective reaction than another route. Accordingly, the described methods are merely exemplary and are in no way limiting.

The dose administered to an animal, particularly human and other mammals, in accordance with the present invention should be sufficient to effect the desired response. Such responses include reversal or prevention of the bad effects of the disease for which treatment is desired or to elicit the desired benefit One skilled in the art will recognize that dosage will depend upon a variety of factors, including the age, species, condition or disease state, and body weight of the animal, as well as the source and extent of the disease condition in the animal. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the individual.

The following examples further illustrate the present invention but, of course, should not be construed as in any way limiting its scope. In the examples, unless otherwise noted, compounds were characterized and resonances assigned by 300 MHz proton nuclear magnetic resonance mass spectroscopy using a Varian GEMINI-300 FT-NMR spectrometer. Also, unless noted otherwise, chemical shifts are expressed as ppm downfield from tetramethylsilane. Synthetic intermediates were characterized by chemical ionization mass spectrometry ($NH_3$) and adenosine derivatives by fast atom bombardment mass spectrometry (positive ions in a noba or m-bullet matrix) on a JEOL SX102 mass spectrometer. Low resolution CI—$NH_3$ (chemical ionization) mass spectra were carried out with Finnigan 4600 mass spectrometer and high-resolution EI (electron impact) mass spectrometry with a VG7070F mass spectrometry at 6 kV. Elemental analysis was performed by Atlantic Microlab Inc. (Norcross, Ga.). NMR and mass spectra were consistent with the assigned structure.

EXAMPLE 1

In all of the potent adenosine agonists previously developed, the ribose moiety is present, and consequently, these agonists are subject to deglycosylation and other pathways of metabolic degradation in vivo. In order to design non-glycosyl adenosine agonists and thereby increase biological stability and potential receptor selectivity, carbocyclic modifications of the ribose moiety have been introduced. In previous studies of adenosine analogues it was found that if adenosine derivatives having carbocyclic modifications of the ribose ring (compounds 1-4, below) bind to adenosine receptors it is only with greatly reduced affinity.

In the present study we have incorporated a complex carbocyclic modification of ribose for use with adenosine agonists. This modification, wherein only one isomeric form retains high affinity and receptor selectivity, is the "methanocarba" ring. In this modification a fused cyclopropane ring constrains the accompanying cyclopentane moiety to mimic the conformation of a rigid furanose ring. The furanose ring of nucleosides and nucleotides in solution is known to exist in a rapid, dynamic equilibrium between a range of Northern and opposing Southern conformations as defined in the pseudorotational cycle. For methanocarba analogues, the bicyclo [3.1.0]hexane ring can constrain the cyclopentane ring into a N-, 2'-exo envelope pucker, and a S-, 3' exo form.

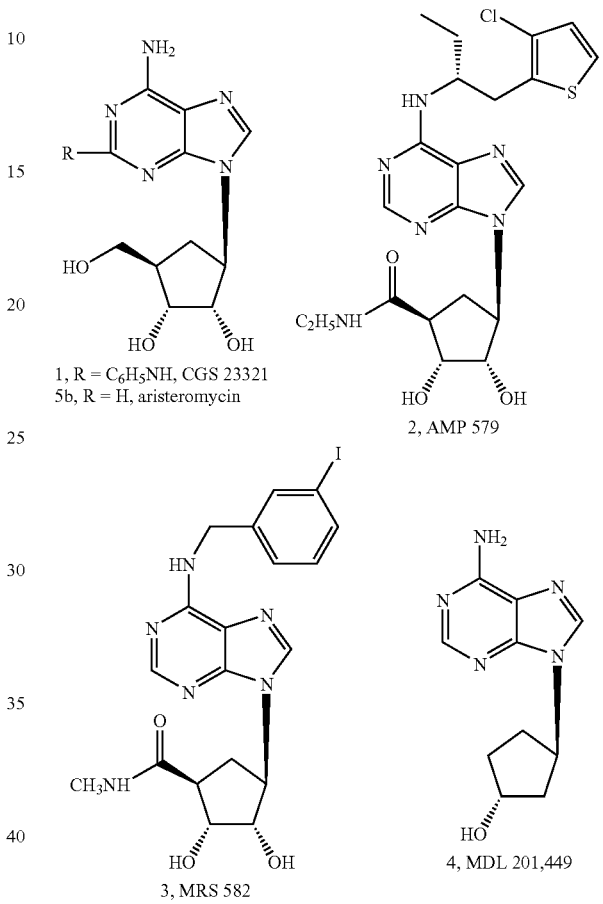

1, R = $C_6H_5NH$, CGS 23321
5b, R = H, aristeromycin
2, AMP 579
3, MRS 582
4, MDL 201,449

These two extreme forms of ring pucker usually define biologically active conformations. This example shows that nucleoside binding to P1-(adenosine) receptors, is favored when the fixed ring-twist conformation is in the N— conformation.

Chemical Synthesis.

Nucleosides and synthetic reagents were purchased from Sigma Chemical Co. (St. Louis, Mo.) and Aldrich (St. Louis, Mo.). 2,6-Dichloropurine was obtained from Sigma. m-iodobenzyl bromide was purchased from Aldrich (St. Louis, Mo.). 4-(6-Aminopurin-9-yl)-1-hydroxymethyl-bicyclo[3.1.0] hexane-2,3-diol (1) and compounds 5c and 5d were obtained from Dr. Victor Marquez. Compounds 7a and 9a were synthesized in our laboratory.

The synthetic strategy used in this example is shown below. The synthesis of N6-substituted N-methanocarba adenosine derivatives optimized for interaction with A1 (CP=cyclopentyl) or A3 (IB=3-iodobenzyl) receptors. Reagents: a) DEAD, $Ph_3P$; b) MEOH, rt; c) $BCl_3$; d) H2/Pd; e) 3-iodobenzyl bromide, 50° C., DMF, 2 days; f) $NH_4OH$, MEOH, 80° C., 3 days.

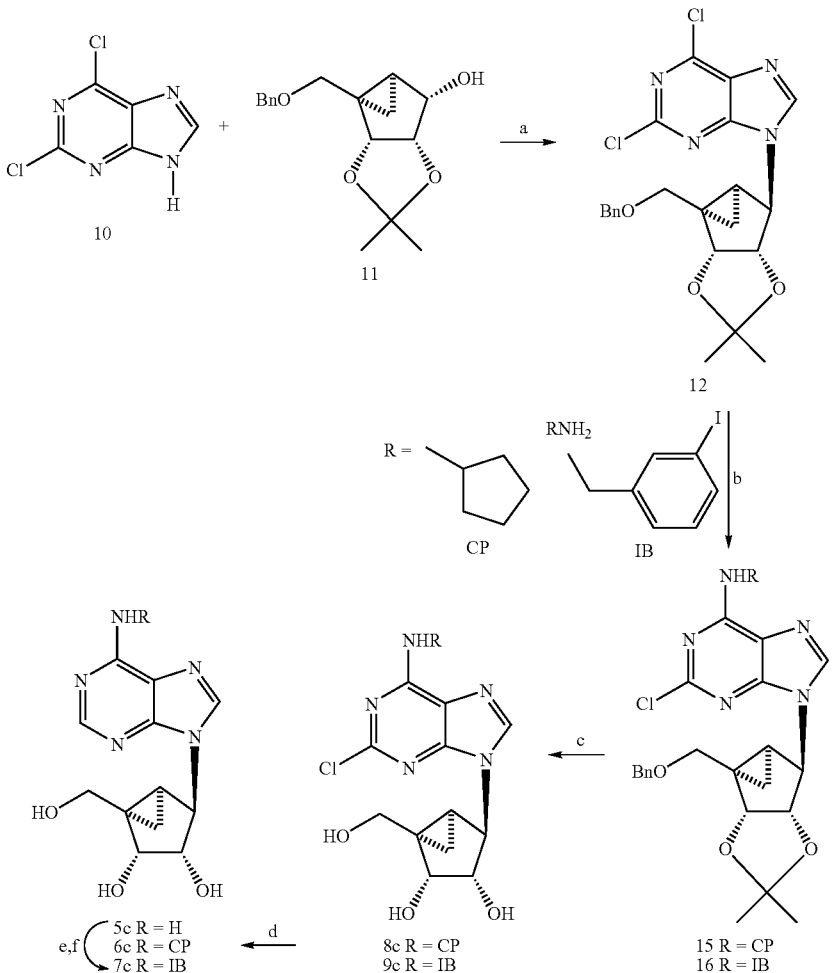

(1'R, 2R, 3'R, 4'R, 1'aR)-2,3-(dihydroxy)-4-(hydroxymethyl)-1-(6-cyclopentylaminopurine-9-yl)bicyclo(3.1.0)hexane) (6c)

A solution of 8c (4 mg, 0.01 mmol) in methanol (0.5 ml) was hydrogenated at atmospheric pressure over 10% Pd/C (1 mg) to furnish the product 6c (83% yield). H'NMR (CD$_3$OD): δ 0.7-0.8 (m, 1H, 6'-C$\underline{H}$H), 1.46-1.88 (m, 1OH, 6'CH$\underline{H}$, 1'aH, 4CH$_2$), 2.01-2.20 (m, 1H, NCH), 3.34 (d, 1H, J=9.77 Hz, 5'CHH), 3.88 (d, 1H, J=6.84 Hz, 3'CH), 4.26 (d, 1H, J=9.77 Hz, 5'CH$\underline{H}$), 4.66-498 (m, 2H, 2'CH, 1'CH), 8.28 (s, 1H, 2CH), 8.5 (s, 1H, 8CH). HRMS(FAB): Cal: 346.1879 Found: 346.1879

(1'R, 2'R, 3'R, 4'R)-2,3-(dihydroxy)-4-(hydroxymethyl)-1-(6-(3-idobenzylamino)purine-9-yl)cyclopentane (7b)

A mixture of aristeromycin (3.5 mg, 0.013 mmol) and 3-iodobenzybromide (12 mg, 0.039 mmol) in anhydrous DMF was heated for 3 days, and solvent was removed under vacuum. The excess 3-iodobenzylamine was removed from the reaction mixture by adding ether to the reaction mixture, and stirring was continued for 5 min. followed by decantation of the supernatant ether phase. The residue was dried, suspended in methanol (1 ml) and ammonium hydroxide (0.5 ml), and heated at 80° C. in a closed tube for 1 h. Solvent was removed under vacuum, and the residue obtained was purified by flash column chromatography using 7/3 chloroform/methanol to furnish 3.0 mg (47%) of the product.

H$^1$NMR(CD$_3$OD) δ 1.86-1.96 (m, 1H, 1'C$\underline{H}$H), 2.14-2.30 (m, 1H, 1'CH$\underline{H}$), 2.38-2.48 (m, 1H, 4'CH), 3.3-3.38 (m, 1H, 5'C$\underline{H}$H), 3.67 (d, 1H, J=6.84 Hz, 5'CH$\underline{H}$), 3.96-4.06 (m, 1H, 3'CH), 4.43-4.48 (m, 1H, 2'CH), 4.73-4.82 (m, 1H, 1'CH), 5.26 (s, 2H, ArCH$_2$), 7.12 (t, 1H, J=7.82 Hz, ArH), 7.32 (d, 1H, J=7.82 Hz, ArH), 7.66 (d, 1H, J=7.82 Hz, ArH), 7.73 (s, 1H, ArH), 8.06 (s, 1H, 2CH). 8.08 (s, 1H, 8CH).

Preparation of 4-[6-(3-iodobenzylamino)-purin-9-yl]-1-hydroxymethyl-bicyclo[3.1.0]hexane-2,3-diol (7c, (N)-Methanocarba-N$^6$-(3-iodobenzyl)adenosine) by Dimroth rarrangement:[1]

To a solution of 4-(6-amino-purin-9-yl)-1-hydroxymethyl-bicyclo[3.1.0]hexane-2,3-diol (5c, 20 mg, 0.0721 mmol) in DMF (0.5 mL) was added m-iodobenzyl bromide (64 mg, 0.216 mmol), and the mixture was stirred at 50° C. for 2 days. DMF was then removed under a stream of N$_2$. To the resulting syrup 0.5 mL of acetone and 1 mL of ether were added and the syrup solidified. The solvents were removed by decantation, and again ether was added and removed. The solid was dried and dissolved in 1 mL MEOH. NH$_4$OH (1.5 mL) was added and the mixture was stirred at 80° C. for 3 days. After cooling down to room temperature, the solvents were removed under reduced pressure and the residue was purified by preparative TLC (silica 60; 1 000 μm; Analtech, Newark, Del.; ethyl acetate-i-PrOH—H$_2$O (8:2:1)) to give 26 mg of the product (7c), yield: 73%. $^1$H NMR (CDCl$_3$): δ 0.82 (t, J=6.0 Hz, 1 H), 1.41 (t, J=4.8 Hz, 1 H), 1.72 (dd, J=8.5, 6.0 Hz, 1 H), 3.36 (d, J=10.8 Hz, 1 H), 4.05 (d, J=6.9 Hz, 1 H), 4.33 (m, 1 H), 4.80-4.88 (m, 3 H), 5.21 (d, J=6.9 Hz, 1 H), 6.25 (m, br, 1), 7.07 (t, J=7.8 Hz, 1 H), 7.35 (d, J=7.8 Hz, 1 H), 7.61 (d, J=7.8 Hz, 1 H), 7.74 (s, 1), 7.93 (s, 1 H), 8.33 (s, 1 H). MS(FAB): m/z 494 (M$^+$+I).

(1'R, 2'R, 3'R, 4'R, 1'aR,)-2,3-(dihydroxy)-4-(hydroxymethyl)-1-(2-chloro-6-cyclopentylaminopurine-9-yl)bicyclo(3.1.0)hexane) (8c):

To a solution of 15 (36 mg, 0.076 mmol) in anhydrous dichloromethane was added BCl$_3$ (1M solution in dichloromethane, 0.23 ml, 0.23 mmol) at 0° C. The reaction mixture was warmed to room temperature and stirred for 10 min. To this mixture was added methanol (1 ml) followed by ammonium hydroxide (0.5 ml). The mixture was concentrated under vacuum, and the residue obtained was purified by flash column chromatography using 9/1 chloroform-1/methanol as eluent to furnish 14 mg of the product 8c (48% yield) as a solid.

H$^1$NMR(CDCl$_3$): δ.o.65-0.9 (m, IH, 6'CHH), 1.1-1.4 (m, 2H, 6'CHH, 1'aH), 1.4-1.9 (m, 8H, 4CH$_2$), 2.0-2.2 (m, 1H, N$^6$CH), 3.34 (d, 1H, J=7.2 Hz, 5'CHH), 3.97 (d, 1H, J=4.6 Hz, 3'CH), 4.25 (d, 1H, J=7.2 Hz, 5'CHH), 4.687 (s, 1H, 1'CH), 5.11 (d, 1H, J 4.6, 2'CH), 7.85 (s, 1H, 8CH). HRMS(FAB): Cal: 380.1489 found: 380.1498

(1'R, 2'R, 3'R, 4'R, 1'aR)-2,3-(dihydroxy)-4-(hydroxymethyl)-1-(2-chloro-6-(3-idobenzylamino)purine-9-yl)bicyclo(3.1.0)hexane) (9c) was synthesized by the same method as 8c in 53% yield.

H$^1$NMR(CD$_3$OD): δ 0.70-0.78 (m, 1H, 6'CHH), 1.50-1.63 (m, 2H, 6, CHH, 1'aH), 3.33 (d, 1H, J=11.72 Hz, 5'CHH), 3.88 (d, 1H, J=6.84 Hz, 3'CH), 4.26 (d, 1H, J=11.72 Hz, 5'CH H), 4.71-4.83 (m, 2H, 1'CH, 2'CH), 7.1 (t, 1H, J=7.82 Hz, ArH), 7.40 (d, 1H, J=7.82 Hz, ArH), 7.61 (d, 1H, 7.82 Hz, ArH), 7.78 (s, 1H, ArH), 8.54 (s, 1H, 8CH). HRMS(FAB): Cal: 528.0299 Found: 528.0295

(2R, 3R, 4R, 1'aR, 1S)-2,3-(O-isopropylidine)-4-(methylenebenzyloxy)-1-(2,6dichloropurine-9-yl)bicyclo(3.1.0)hexane) (12)

To a solution of triphenyl phosphine (260 mg, 1 mmol) in anhydrous THF (2 ml) was added DEAD (0.16 ml, 1 mmol) dropwise at 0° C., and stirring was continued for 20 min. To this solution was added a solution of 2,6-dichloropurine in THF (4 ml) followed by the addition of 11 (145 mg, 0.5 mmol) in THF (4 ml). The reaction mixture was warmed to room temperature, and stirring was continued for 6 h. Solvent was evaporated under vacuum, and the residue obtained was purified by flash chromatography using 7/3 petroleumether/ethylacetate as eluent to furnish 141 mg of the product (12) (70% yield) as a gum.

H$^1$NMR (CDCl$_3$): ∂ 1.0 (m,1H, 6'CHH), 1.24 (s, 3H, CH$_3$), 1.27-1.38 (m, 1H, 6'CHH), 1.55 (s, 3H, CH$_3$),1.62 (dd, 1H, J=4.88, 9.77 Hz, 1'aH), 3.34 (d, 1H, J=9.77 Hz, 5'CHH), 3.97 (d, 1H, J=9.77 Hz, 5'CHH), 4.50 (d, 1H, J=6.84 Hz, 3'CH), 4.57-4.68 (qAB, 2H, J=12.7 Hz, ArCH$_2$), 5.17 (s, 1H, 1'CH), 5.32 (d, 1H, J=6.84 Hz, 2'H), 7.27.4 (m, 5H, Ar), 8.63 (s, 1H, 8CH).

(2R, 3R, 4R, 1'aR, 1S)-2,3-(O-isopropylidine)-4-(methylenebenzyloxy)-1-(2-chloro-6-cyclopentylaminopurine-9-yl)bicyclo(3.1.0)hexane) (15):

To a solution of 12 (42 mg, 0.105 mmol) in methanol (2 ml) was added cyclopentylamine at room temperature, and stirring was continued for 6 hr for complete reaction. Solvent was removed under vacuum, and the residue obtained was purified by flash column chromatography using 7/3 petroleum ether/ethylacetate as eluent to furnish 45 mg of the product 15 (90% yield) as a gum.

H$^1$NMR(CDCl$_3$): δ 0.92-0.96 (m, 1H. 6'CHH), 1.14-1.01 (m, 1H, 6'CHH), 1.23 (s, 3H, CH$_3$),1.42-1.81 (m, 9H, 1'aH, 4CH$_2$),1.54 (s, 3H, CH$_3$), 2.08-2.21 (m, 1H, N$^6$CH), 3.44 (d, 1H, J=9.76 Hz, 5'CHH), 3.90 (d, 1H, J=9.76 Hz, 5'CHH), 4.51 (d, 1H, J=6.84 Hz, 3'CH), 4.57-4.67 (qAB, 2H, J=12.7 Hz, ArCH$_2$), 5.04 (s, 1H, 1'CH), 5.32 (d, 1H, J=6.84 Hz, 2'CH), 7.2-7.4 (m, 5H, Ar), 8.18 (s, 1H, 8CH).

(1'R, 2'R, 3'R, 4'R, 1'aR)-2,3-(O-isopropylidine)-4-(methylenebenzyloxy)-1-(2-chloro-6-(3-idobenzylamino)purine-9-yl)bicyclo(3.1.0)hexane) (16) was synthesized in 70% yield by the same method as 15, except using 3-iodobenzylamine hydrochloride and two equivalents of triethylamine.

H$^1$NMR(CDCl$_3$): δ 0.87-0.91 (m, 1H, 6'CHH), 1.10-1.29 (m, 1H, 6'CHH), 1.17 (s, 3H, CH$_3$),1.42-1.56 (m, 1H, 1'aH), 1.47 (s, 3H, CH$_3$), 3.37 (d, 1H, J=9.77 Hz, 5'CHH), 3.84 (d, 1H, J=9.77 Hz, 5'CHH), 4.44 (d, 1H, J=6.84 Hz, 3'CH), 4.50-4.60 (qAB, 2H, J=11.72 Hz, ArCH$_2$), 4.70 (bs, 1H, NH), 4.98 (s, 1H, 1'CH), 5.24 (d, 1H, J=6.84 Hz, 2'CH), 7.0 (t, 1H, J=7.82 Hz, ArH), 7.2-7.34 (m, 6H, ArH), 7.55 (d, 1H, J=7.82, ArH), 7.65 (s, 1H, ArH), 8.08 (s, 1H, 8CH).

Pharmacological Analyses.

Materials

F-12 (Ham's) medium, fetal bovine serum (FBS) and penicillin/streptomycin were from Gibco BRL (Gaithersburg, Md.). [$^{125}$I]AB-MECA (1000 Ci/mmol) and [$^{35}$S]guanosine 5'-(γ-thio)triphosphate (1000-1500 Ci/mmol) were from DuPont NEN (Boston, Mass.). Adenosine deaminase (ADA) was from Boehringer Mannheim (Indianapolis, Ind.). All other materials were from standard local sources and of the highest grade commercially available.

Cell Culture and Membrane Preparation

CHO cells stably transfected with either human A$_1$ or A$_3$ receptors (gift of Dr. Gary Stiles and Dr. Mark Olah, Duke University Medical Center) were cultured as monolayers in medium supplemented with 10% fetal bovine serum. Cells were washed twice with 10 ml of ice-cold phosphate buffered saline, lysed in lysis buffer (10 mM Tris.HCl buffer, pH 7.4, containing 2 mM MgCl$_2$ and 0.5 mM EDTA), and homogenized in a Polytron homogenizer in the presence of 0.2 U/ml adenosine deaminase. The crude membranes were prepared by centrifuging the homogenate at 1000×g for 10 min followed by centrifugation of the supernatant at 40,000×g for 15 min. The pellet was washed once with the lysis buffer and recentrifuged at 40,000×g for 15 min. The final pellets were resuspended in 50 mM Tris.HCl buffer, pH 7.4, containing 10 mM MgCl$_2$ and 0.1 mM EDTA and stored at −70° C.

Radioreceptor Binding

Determination of binding to adenosine A$_1$, A$_{2A}$ and A$_{2B}$ receptors was carried out as reported. Determination of A$_3$ adenosine receptor binding was carried out using [$^{125}$I]AB-MECA. Briefly, aliquots of crude transfected CHO cell membranes (approximately 40 μg protein/tube) were incubated with 0.5 nM [$^{125}$I]AB-MECA, 10 mM MgCl$_2$, 2 units/ml adenosine deaminase, 50 mM Tris.HCl (pH 7.4) at 37° C. for 60 min. The total volume of the reaction mixture was 125 μl. Bound and free ligands were separated by rapid filtration of the reaction mixture through Whatman GF/B glass filters. The filters were immediately washed with two 5 ml-portions of ice-cold 50 mM Tris.HCl buffer (pH 7.4). The radioactivity bound to the filters was determined in a Beckman gamma counter. Specific binding was defined as the amount of the radioligand bound in the absence of competing ligand minus the amount of that bound in the presence of 100 μM NECA. Ki-values were calculated using the $K_d$ for [$^{125}$I]AB-MECA binding of 0.56 nM.

Determination of [3'S]GTPγS Binding

[$^{35}$S]GTPγS binding was determined by the method of Lorenzen et al. The incubation mixture contained in a total volume of 125 μl, 50 mM Tris.HCl (pH 7.4), 1 mM EDTA, 10 mM $MgCl_2$, 10 μM guanosine 5'-diphosphate, 1 mM dithiothreitol, 100 mM NaCl, 0.2 units/ml adenosine deaminase, 0.16 nM [$^{35}$S] GTPγS (about 50,000 cpm) and 0.5% BSA. The CHO cell membranes expressing $A_1$ or $A_3$ receptors were preincubated with the above-mentioned assay mixture at 37° C. for 1 h and further incubated for 1 hr after the addition of [$^{35}$S]GTPγS. Incubations were terminated by rapid filtration of the samples through glass fiber filters (Whatman GF/B), followed by two 5 ml washes of the same buffer. After transferring the filters into a vial containing 3 ml of scintillation cocktail, the radioactivity was determined in a scintillation counter.

Data Analysis. Analyses of saturation binding assays and concentration-response curves were carried out using the GraphPad Prism (GraphPad Software Inc., San Diego, Calif.). Comparisons between groups were carried out using the unpaired Student's test.

Results

Chemical Synthesis

The methanocarbocyclic 2'-deoxyadenosine analogues, shown below in Table 1, in which a fused cyclopropane ring constrains the cyclopentane ring into a rigid envelope configuration of either a N— or S— conformation, were synthesized in a manner similar as shown above. The N-methanocarba analogues of various $N^6$-substituted adenosine derivatives, including cyclopentyl and iodobenzyl, in which the parent compounds are potent and selective agonists at either $A_1$ or $A_3$ receptors, respectively, were prepared. 2,6-Dichloropurine, 10, was condensed with the cyclopentyl derivative, 11, using the Mitsunobu reaction, followed by substitution at the 6-position and deprotection to give 8c or 9e. The 2-chloro substitution of compound 8c was removed by catalytic reduction to give 6c. This allowed the incorporation in the N-configuration series of the 2-chloro modification of adenine, which was of interest for its effect on adenosine receptor affinity. An $N^6$-(3-iodobenzyl) group could also be introduced in either aristeromycin, 5b, or N-methanocarba-adenosine, 5c, by the Dimroth rearrangement, to give 7b and 7c.

Biological Activity

A pair of methanocarba analogues of adenosine, 5c and 5d, corresponding to N— and S— conformations of ribose, were tested in binding assays, the results of which are shown in Table 1 below, at four subtypes of adenosine receptors. The more synthetically challenging S-isomer (5d) was available only as the racemate and therefore was tested as such. At rat A1, rat A2A, and human A3 subtypes, the N-analogue proved to be of much higher affinity than the S-analogue. At the human A2B receptor, binding was carried out using [3H]ZM 241,385, however the affinity was too weak to establish selectivity for a specific isomer. Affinity of N-methanocarba-adenosine, 5c, vs. adenosine, 5a, was particularly enhanced at the A3 receptor subtype, for which the ratio of affinities of N— to S-analogues was 150-fold. Although a poor substrate for adenosine deaminase (ADA), the binding curve for 5c was shifted in the presence of ADA, therefore the affinity values for 5c and 5d obtained in the absence of ADA are entered in Table 1, below. The South confomer, 5d, is even a worse substrate of ADA (100-fold less) which explains why the curves in the presence and absence of ADA for 5d are virtually the same. Aristeromycin, 5b, bound weakly to adenosine receptors, with slight selectivity for the $A_{2A}$ subtype. Compound 5c was more potent than aristeromycin, 5b, in binding to A1 (4-fold) and A3 (4500-fold) adenosine receptors.

Compounds 6c and 8c are patterned after A1 receptor-selective agonists, while compounds 7c and 9c are patterned after A3 receptor-selective agonists. Compounds 6 and 7 are unsubstituted at the 2-position, while compounds 8 and 9 contain the potency enhancing 2-chloro substituent. The N6-cyclopentyl N-methanocarba derivative, 6c, based on CPA, 6a, maintained high selectivity for A1 receptors, although the affinity of 6c at rat A1 receptors was 3-fold less than for 6a. In one series it was possible to compare ribose, cyclopentyl, and N-methanocarba derivatives having the same N6-substitution. The N6-(3-iodobenzyl) derivative, 7c, based on a 5'-hydroxy analogue, 7a, of IB-MECA, with a Ki value of 4.1 nM was 2.3-fold more potent at A3 receptors than the ribose-containing parent. Thus, the selectivity of 7c for human A3 versus rat AI receptors was 17-fold. The aristeromycin analogue, 7b, was relatively weak in binding to adenosine receptors.

Among 2-chloro-substituted derivatives, the N-methanocarba analogue, 8c, was less potent at A1 and A2A receptors than its parent 2-chloro-N6-cyclopentyladenosine, 8a, and roughly equipotent at A3 receptors. Thus, 8c was 53-fold selective in binding to rat A1 vs. human A3 receptors. The N-methanocarba analogue, 9c, of 2-chloro-N6-(3iodobenzyl)adenosine, 9a, had Ki values (nM) of 141, 732, and 2.2 at A1, A2A, and A3 receptors, respectively. Thus, the 2-chloro group slightly enhanced affinity at A3 receptors, while reducing affinity at A1 receptors.

The receptor binding affinity upon replacement of ribose with the N-methanocarba moiety was best preserved for the A3 subtype, at which differences were small. At A1 receptors the loss of affinity for structures 6-9 was between 3- and 8-fold. At A2A receptors the loss of affinity was between 6- and 34-fold.

The agonist-induced stimulation of binding of guanine nucleotides to activated G-proteins has been used as a functional assay for a variety of receptors, including adenosine receptors. Binding of [$^{35}$S]GTP-γ-S was studied in membranes prepared from CHO cells stably expressing human A1 or A3 receptors (Table 2). The non-selective adenosine agonist NECA (5'-N-ethyluronamidoadenosine) caused a concentration-dependent increase in the level of the guanine nucleotide bound. Compound 6c was highly selective and a full agonist at human A1 but not rat A1 receptors. Both 7c and 9c stimulated the binding of [$^{35}$S]GTP-γ-S, however the maximal stimulation was significantly less than that produced by either NECA or N6(3-iodobenzyl)adenosine, 7a, both being full A3 agonists. Compounds 7c and 9c resulted in relative stimulation of [$^{35}$S]GTP-γ-S binding of only 45% and 22%, respectively, indicating that the efficacy of the N-methanocarba analogue at A3 receptors was further reduced upon 2-chloro modification. The potency of compounds 7c and 9c, indicated by the EC50 values in this functional assay, was greater than the potencies of either NECA or compound 7a (Table 2). Thus, the N-methanocarba N6-(3-iodobenzyl) analogues appear to be highly potent and selective partial agonists at human A3 receptors

TABLE I

Affinities of Adenosine Derivatives[1]

$R_1 =$ structures a, b, c, d and purine scaffolds (5-7, 8-9)

| Compound | R' | R | $RA_1{}^a$ | $RA_{2A}{}^b$ | $hA_3{}^c$ |
|---|---|---|---|---|---|
| 1a CPA | H | cyclopentyl | 0.59 | 462 | 274 ± 20  240 (r) |
| 1B 1781 | H | cyclopentyl | 5.06 ± 0.51 | 6800 ± 1800 | 170 ± 51 |
| 1c 1783 | H | cyclopentyl | 5110 ± 790 | 15% at 10 μM | |
| 2a IB0-ADO, 541 | H | 3-iodobenzyl | 20.0 ± 8.5 | 17.5 ± 0.5 | 9.5 ± 1.4 (r) |
| 2b 1743 | H | 3-iodobenzyl | 69.2 ± 9.8 | 601 ± 236 | 4.13 ± 1.76 |
| 3a CCPA | Cl | yclopentyl | 0.6 | 950 | 237 (r) |
| 3b 1761 | Cl | cyclopentyl | 8.76 ± 0.81 | 3390 ± 520 | 466 ± 58 |
| 3c 1782 | Cl | cyclopentyl | 3600 ± 780 | 45 ± 5% at 100 μM | |
| 4a 542 | Cl | 3-iodobenzyl | 18.5 ± 4.7 | 38.5 ± 2.0 | 1.41 ± 0.17 (r) |
| 4b 1760 | Cl | 3-iodobenzyl | 141 ± 22 | 732 ± 207 | 2.24 ± 1.45 |
| 4c 1784 | Cl | 3-iodobenzyl | 8730 ± 370 | 25,400 ± 3800 | |

| Compound | $R_2$ | $rA_1{}^a$ | $rA_{2A}{}^b$ | $hA_{2B}{}^b$ | $hA_3{}^b$ | $A_1/A_3$ |
|---|---|---|---|---|---|---|
| 5a | H | Estd. $10^d$ | estd. $30^d$ | <10% at 100 μM | estd. 1000 $(r)^{d,e}$ | 100 |
| 5b | H | 6260 ± 730 | 2150 ± 950 | 47,300 ± 10,600 | 20,000 ± 7900 $(r)^e$ | 0.31 |
| 5c | H | 1680 ± 80 | 22,500 ± 100 $(h)^{e,f}$ | 35 ± 2% at 50 μM$^f$ | 404 ± 70$^f$ | 4.2 |
| 5d (racemic) | H | 15% at 100 μM | >100,000 $(h)^{e,f}$ | 20 ± 4% at 50 μM$^f$ | 62,500 ± 2900$^f$ | >1 |
| 6a | CP | 1.50 ± 0.51 | 857 ± 163 | 21,200 ± 4300 | 274 ± 20,240 $(r)^e$ | 0.0055 |
| 6c | CP | 5.06 ± 0.51 | 6800 ± 1800 | 139k ± 19k | 170 ± 51 | 0.030 |
| 7a | IB | 20.0 ± 8.5 | 17.5 ± 0.5 | 3570 ± 100 | 9.5 ± 1.4 $(r)^e$ | 2.1 |
| 7b | IB | 25,900 ± 1600 | <10% 100 μM | n.d. | 1960 ± 370 | 13 |
| 7c | IB | 69.2 ± 9.8 | 601 ± 236 | 12,100 ± 1300 | 4.13 ± 1.76 | 17 |
| 8a | CP | 1.33 ± 0.19 | 605 ± 154 | 20,400 ± 1200 | 237 $(r)^e$ | 0.0056 |
| 8c | CP | 8.76 ± 0.81 | 3390 ± 520 | 27 ± 7% at 100 μM | 466 ± 58 | 0.019 |
| 9a | IB | 18.5 ± 4.7 | 38.5 ± 2.0 | 5010 ± 1400 | 1.41 ± 0.17 $(r)^e$ | 13 |
| 9c | IB | 141 ± 22 | 732 ± 207 | 41,000 ± 700 | 2.24 ± 1.45 | 63 |

[1](a) simple carbocyclic, (b) and methanocarba-adenosine, (N)-conformation, (c) and S-conformation, (d) derivatives in radioligand binding assays at rat $A_1$,$^a$ rat $A_{2A}$,$^b$ human $A_{2B}$,$^b$ and human $A_3$ receptors, $^c$ unless noted.$^e$

TABLE II

Effect of ligands to stimulate [$^{35}$S]GTPγS binding to membranes of cells expressing the cloned hA$_1$AR or hA$_3$AR or in rat cerebral cortical membranes containing the A$_1$AR

| Ligand | cloned hA$_1$AR EC$_{50}$ (nM)$^a$ | % Maximal Stimulation$^c$ | rA$_1$AR EC$_{50}$ (nM)$^a$ | % Maximal Stimulation$^c$ | cloned hA$_3$AR EC$_{50}$ (nM)$^a$ | % Maximal Stimulation$^c$ |
|---|---|---|---|---|---|---|
| NECA | n.d. | | n.d. | | 155 ± 15 | 100 |
| 6a | 4.15 ± 0.90 | 100 | 20.3 ± 13.1 | 100 | 7980 ± 60 | 100 |
| 6c | 21.5 ± 2.3 | 102 ± 1 | 100 ± 17 | 75 ± 6 | >10,000 | 14 ± 2% at 10 μM |
| 7a | 43.1 ± 10.4 | 91 ± 1 | 340 ± 98 | 95 ± 4 | 5.16 ± 0.71 | 100 |
| 7b | >10,000 | 5 ± 2% at 10 μM | n.d. | | >10,000 | 15 ± 5% at 10 μM |
| 7c | 218 ± 18 | 86 ± 2 | 940 ± 114 | 55 ± 5 | 0.70 ± 0.16 | 45.3 ± 6.8 |
| 8c | 31.2 ± 3.3 | 97 ± 1 | 145 ± 35 | 96 ± 2 | n.d. | |
| 9c | 142 ± 24 | 91 ± 1 | 684 ± 75 | 48 ± 3 | 0.67 ± 0.19 | 22.0 ± 2.8 |

$^a$EC$_{50}$ for stimulation of basal [$^{35}$S]GTP-γ-S binding by agonists in membranes from transfected CHO cells (±S.E.M.), n = 3.
n.d. not determined.

Discussion

Nearly all of the thousands of known adenosine agonists are derivatives of adenosine. Although molecular modeling of adenosine agonists has been carried out, there has been no direct evidence from this for a conformational preference of the ribose ring in the receptor binding site. In the present study, methanocarba-adenosine analogues have defined the role of sugar puckering in stabilizing the active receptor-bound conformation. The S-methanocarba analogue of adenosine, 5d, was only weakly active, presumably because of a disfavored conformation that decreases receptor binding. In contrast, the methanocarba analogues constrained in the N-conformation, e.g. 5c-9c, displayed high receptor affinity, particularly at the A3 receptor. In binding assays at A1, A2A, and A3 receptors, N-methanocarba-adenosine proved to be of higher affinity than the S-analogue, with an N:S-affinity ratio of 150 at the human A3 receptor. Thus, the biological potency and efficacy of this series of nucleosides appears to be highly dependent on ring puckering, which in turn would influence the orientation of the hydroxyl groups within the receptor binding site.

The structure activity relationship (SAR) of adenosine agonists indicates that the ribose ring oxygen may be substituted with carbon, as in 5b and 7b, however much affinity is lost. As demonstrated with the aristeromycin derivative, 7b, simple carbocyclic substitution of the ribose moiety of otherwise potent, N6-subsituted adenosine agonists greatly diminishes affinity, even in comparison to aristeromycin, 5b.

In comparison to the ribose analogues, the N-methanocarba N6-subsituted adenosine agonists were of comparable affinity at A3 receptors, but less potent at A1, A2A, and A2B receptors. The N-methanocarba N6-cyclopentyl derivatives were A1 receptor-selective and maintained high efficacy at human recombinant but not rat brain A1 receptors, as indicated by stimulation of binding of [$^{35}$S]GTPγS. This may be related to either species differences or heterogeneity of G proteins, since the degree of agonist efficacy of a given compound may be highly dependent on the receptor-associated G protein. N-Methanocarba N6-(3-iodobenzyl)adenosine and the 2-chloro derivative had Ki values of 4.1 and 2.2 nM at A3 receptors, respectively, and were selective partial agonists. As for the ribose parents, additional 2-chloro substitution was favorable for receptor selectivity. However, unlike the ribose forms, efficacy was reduced in N6-(3-iodobenzyl) analogues, such that partial A3 receptor agonists 7c and 9c were produced.

Partial agonists are possibly more desirable than full agonists as therapeutic agents due to potentially reduced side effects in the former. Partial agonists may display in vivo specificity for sites at which spare receptors are present, and the drug would therefore behave with apparent "full" efficacy. Thus, for compounds 7c and 9c, partial agonism combined with unprecedented functional potency at A3 receptors (<1 nM) may give rise to tissue selectivity.

Thus, at least three of the four adenosine receptors favor the N-conformation. For another member of the GPCR superfamily, the P2Y1 receptor, we recently reported that the ribose N-conformation of adenine nucleotides also appears to be preferred at the receptor binding site. Thus, the P1 and at least one of the P2 purinoceptors share the preference for the N-conformation. This may suggest a common motif of binding of nucleoside moieties among these GPCRS. The insights of this conformational preference may be utilized in simulated docking of adenosine agonists in a putative receptor binding site and to design even more potent and selective agents.

At the binding site of ADA, the N-isomer is also preferred, although the carbocyclic adenosine analogues are relatively poor substrates (relative rates of deamination are: 5a, 100; 5b, 0.99; 5c, 0.58; 5d, 0.010. N6-substituted analogues, such as 6c-9c, would not be expected to be substrates for ADA. Other enzymes, such as HIV reverse transcriptase and Herpes thymidine kinase (HSV-1 TK) are also able to discriminate between the two antipodal conformations of restricted methanocarba thymidine analogues.

In conclusion, we have found that the introduction of a methano-carbocyclic modification of the ribose ring of purine agonists represents a general approach for the enhancement of pharmacodynamic and because of the absence of the glycosyl bond, potentially of pharmacokinetic properties. This approach could therefore be applied to the development of cardioprotective, cerebroprotective, and anti-inflammatory agents.

EXAMPLE 2

Introduction

P2 receptors, which are activated by purine and/or pyrimidine nucleotides, consist of two families: G protein-coupled receptors termed P2Y, of which 5 mammalian subtypes have been cloned, and ligand-gated cation channels termed P2X, of which 7 mammalian subtypes have been cloned. The $P2Y_1$ receptor, which is present in the heart, skeletal and various smooth muscles, prostate, ovary, and brain, was the first P2 subtype to be cloned. The nomenclature of P2 receptors and their various ligand specificities is well established.

Nucleotide agonists binding at $P2Y_1$ receptors induce activation of phospholipase C (PLC), which generates inositol phosphates and diacylglycerol from phosphatidyl inositol-(4, 5)-bisphosphate, leading to a rise in intracellular calcium. A $P2Y_1$ receptor antagonist may have potential as an anti-thrombotic agent, while a selective $P2Y_1$ receptor agonist may have potential as an anti-hypertensive or anti-diabetic agent.

Recently, progress in the synthesis of selective P2 receptor antagonists has occurred. Adenosine 3',5'- and 2',5'-bisphosphates were recently shown to be selective antagonists or partial agonists at $P2Y_1$ receptors, and other classes of P2 antagonists include pyridoxal phosphate derivatives, isoquinolines, large aromatic sulfonates related to the trypanocidal drug suramin and various dyestuffs, and 2',3'-nitrophenylnucleotide derivatives. Synthesis of analogues of adenosine bisphosphates has resulted in N6-methyl-2'-deoxyadenosine-3',5'-bisphosphate (1a, MRS 2179), a competitive antagonist at human and turkey $P2Y_1$ receptors, with a KB value of approximately 100 Nm. The presence of an $N^6$-methyl group and the absence of a 2'-hydroxyl group both enhanced affinity and decreased agonist efficacy, thus resulting in a pure antagonist at both turkey and human $P2Y_1$ receptor. The corresponding 2-Cl analogue (1b, MRS 2216) was slightly more potent than 1a as an antagonist at turkey $P2Y_1$ receptors, with an $IC_{50}$ value of 0.22 μM in blocking the effects of 10 nm 2-methylthioadenosine-5'diphosphate (2-MeSADP). MRS2179 (compound 1a) was inactive at $P2Y_2$, $P2Y_4$, and $P2Y_6$ subtypes, at the adenylyl cyclase-linked P2Y receptor in C6 glioma cells and at a novel avian P2Y receptor that inhibits adenylyl cyclase. However, the selectivity of this series of nucleotides for the $P2Y_1$ receptor is not absolute, since 1a also displayed considerable activity at $P2X_1$ receptors ($EC_{50}$ 1.2 μM), but not at $P2Y_{2-4}$ receptors.

In order to move away from the nucleotide structure of 1a and thereby increase biological stability and selectivity for the receptors in the present study, further structural modifications of the ribose moiety have been carried out. We have explored the SAR of these two series and introduced major modifications of the ribose moiety. These modifications include fixing the ring pucker conformation in the carbocyclic series using a bridging cyclopropane ring, ring enlargement with introduction of a nitrogen atom, and ring contraction.

Results

Chemical synthesis

The methanocarbocyclic 2'-deoxyadenosine analogues in which the fused cyclopropane ring fixes the conformation of the carbocyclic nucleoside into a rigid northern or southern envelope conformation, as defined in the pseudoroational cycle, were synthesized as precursors of nucleotides 4 and 5 by the general approach of Marquez and coworkers. Again, the $N^6$-methyl group was introduced by the Dimroth rearrangement, as shown below.

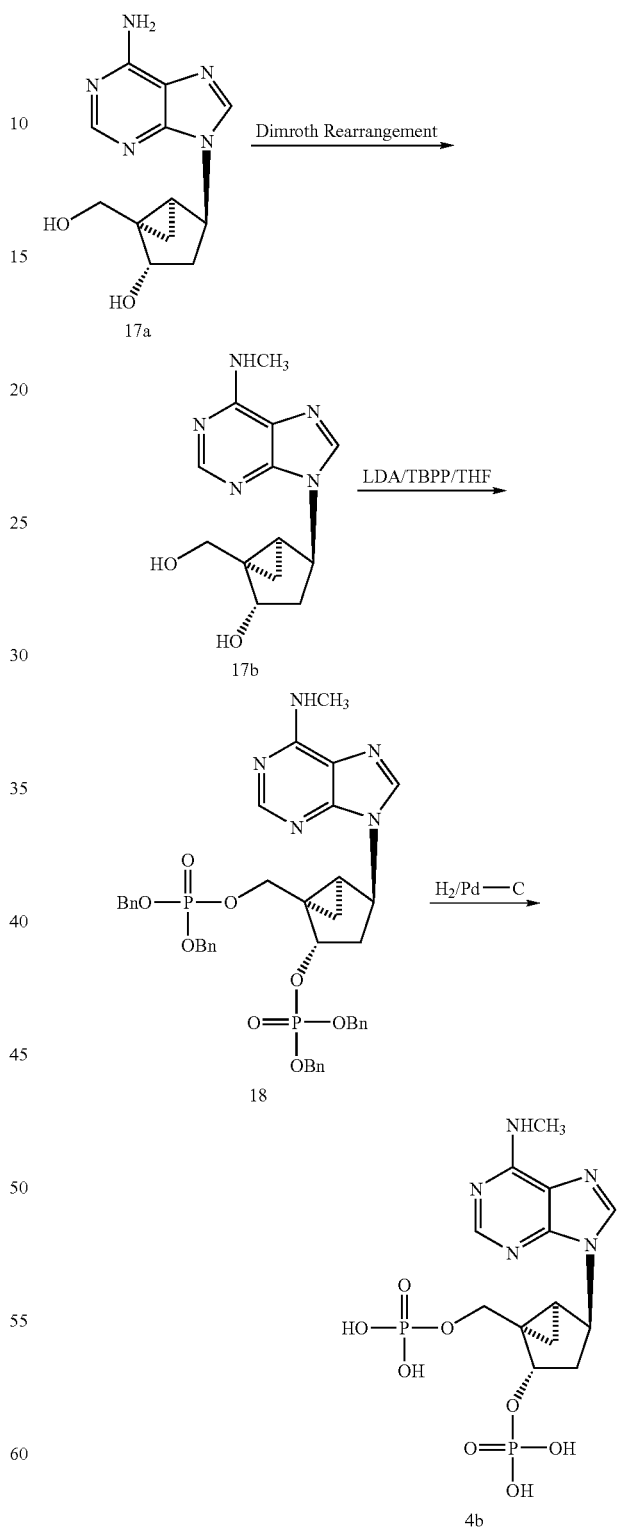

Position adenine modifications were further introduced in the N-configuration series as shown below.

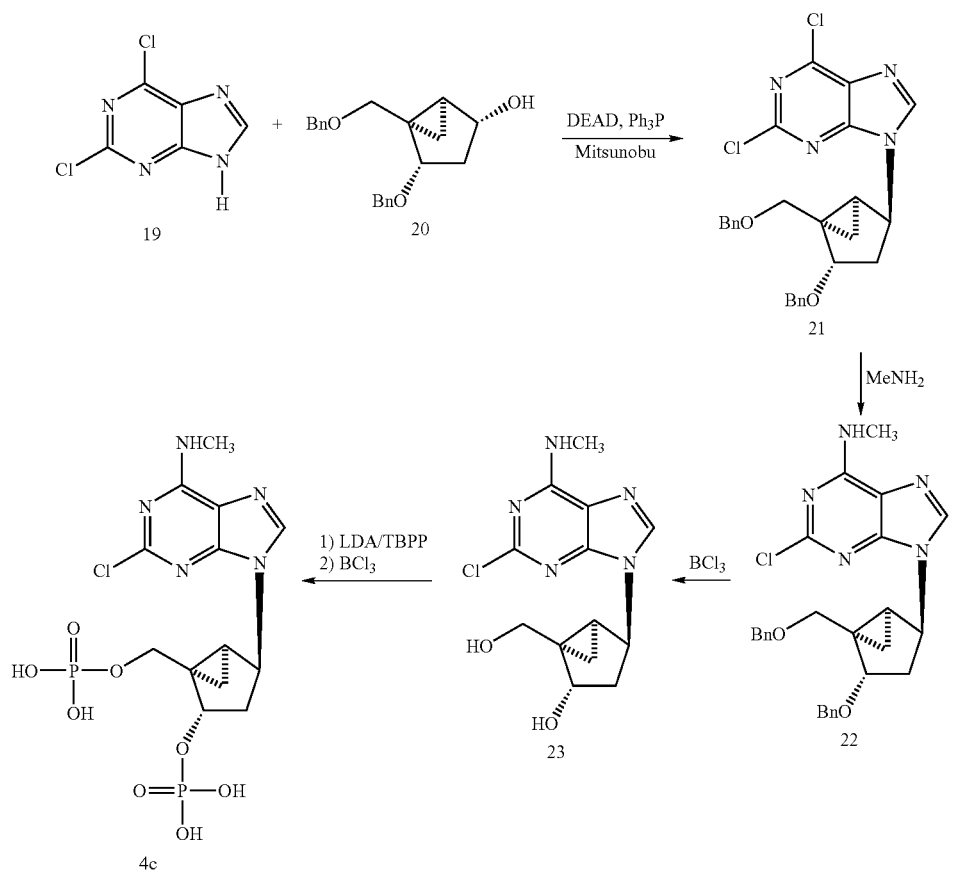

Biological Activity

Adenine nucleotides markedly stimulate inositol lipid hydrolysis by phospholipase C in turkey erythrocyte membranes, through activation of a $P2Y_1$ receptor. The agonist used in screening these analogues, 2-MeSADP, has a higher potency than the corresponding triphosphate for stimulation of inositol phosphate accumulation in membranes isolated from [$^3$H]inositol-labeled turkey erythrocytes.

The deoxyadenosine bisphosphate nucleotide analogues prepared in the present study were tested separately for agonist and antagonist activity in the PLC assay at the $P2Y_1$ receptor in turkey erythrocyte membranes, and the results are reported in Table 3. Concentration-response curves were determined for each compound alone and in combination with 10 nM 2-MeSADP.

Marquez and coworkers have introduced the concept of ring-constrained carbocyclic nucleoside analogues, based on cyclopentane rings constrained in the N-(Northern) and S-(Southern) conformations by fusion with a cyclopropane (methanocarba) ring. In the present studies the series of ring-constrained N-methanocarba derivatives, the 6-NH$_2$ analogues, 4a was a pure agonist of $EC_{50}$ 152 nM and 88-fold more potent than the corresponding S-isomer, 5, also an agonist. Thus, the ribose ring N-conformation appeared to be favored in recognition at $P2Y_1$ receptors. The N$^6$-methy- and 2-chloro-N$^6$-methyl-N-methanocarba analogues, 4b and 4c, were antagonists having $IC_{50}$ values of 276 and 53 nM, respectively.

Molecular Modeling

To better understand the role of the sugar puckering on the human $P2Y_1$ agonist and antagonists activities, we carried out a molecular modeling study of this new generation of ribose-modified ligands. Such modifications include cyclopentyl rings constrained in the N— and S— conformations with cyclopropyl (methanocarba) groups, six-membered rings (morpholino and anhydrohexitol analogues), and cyclobutyl nucleotides. We have recently developed a model of the human $P2Y_1$ receptor, using rhodopsin as a template, by adapting a facile method to simulate the reorganization of the native receptor structure induced by the ligand coordination (cross-docking procedure). Details of the model building are given in the Experimental Section. We have also reported the hypothetical molecular basis for recognition by human $P2Y_1$ receptors of the natural ligand ATP and the new potent, competitive antagonist 2'-deoxy-N$^6$-methyladenosine-3',5'-bisphosphate. Both ATP and 1a are present in the hypothetical binding site with a N-sugar ring conformation. In the present work, the sterically constrained N— and S-methanocarba agonist analogues, 4a and 5, respectively, were docked into the putative binding site of our previously reported $P2Y_1$ receptor model. According to their structural similarity, the cross-docking procedure demonstrated that the receptor architecture found for binding the ATP and 1a was energetically appropriate also for the binding of both 4a and 5. However, N-methanocarba/$P2Y_1$ complex appeared more stable by approximately 20 kcal/mol than S-methanocarba/$P2Y_1$ complex. In the lowest energy docked complex of N-methanocarba agonist in the proposed ligand binding cavity the side chain of Gln307 is within hydrogen bonding distance of the $N^6$ atom at 1.8 Å, and the side chain of Ser314 is positioned at 2.0 Å from the $N^1$ atom and at 3.4 Å from the $N^6$ of the purine ring. As already reported, another three amino acids are important for the coordination of the phosphate groups in the antagonist: Arg128, Lys280 and Arg310. Lys280 may interact directly with both 3'-5'-phosphates (1.7 Å, O3' and 1.7 Å, O5'), whereas Arg128 and Arg310 are within ionic coupling range to both the O2 and O3 atoms of the 5'-phosphate. In molecular modeling studies poor superimposition (rms=1.447) between the — and S-methanocarba agonist analogues has been found inside the receptor binding domain. In particular, the adenine moiety and 5' phosphate of the S-methanocarba derivative are shifted out position relative to with the N-methanocarba isomer, decreasing the stability of the S-methanocarba/$PSY_1$ complex. This fact might be correlated with the difference of their biological activity as seen in Table 4 below.

Using the information that a common binding site could be hypothesized among these deoxyadenosine bisphosphate analogues, a superimposition analysis of the energy-minimized of the more potent antagonists has been performed. In this analysis we have used 1a as a reference compound, and we have defined three matching pairs of atoms, corresponding to $N^1$ atom of the purine ring and the P atoms of both 3' and 5' phosphate groups, to carry out the superimposition analysis. As reported in Table 4, acceptable RMS values have been obtained for all the antagonists compared with the 1a structure. As shown in FIG. 4A, this superimposition study suggested that the two phosphate groups may occupy a common receptor regions, and a general pharmacophore model for bisphosphate antagonists binding to the human $PSY_1$ receptor can be extrapolated.

Discussion

In conclusion the present study has identified new pharmacological probes of $PSY_1$ receptors, including full agonists, partial agonists, and antagonists. The SAR of 1a indicates that the ribose ring oxygen may be readily substituted with carbon. Furthermore, analogues of constrained conformation, e.g. the methanocarba analogues, display enhanced receptor affinity. Additional 2-chloro and $N^6$-methyl substitution is favorable for affinity at $PSY_1$ receptors, and nearly pure antagonism is maintained provided that the $N^6$-methyl group is present.

Thus, the biological potency and efficacy of this series of bisphosphates appears to be highly dependent on subtle conformational factors, which would influence the orientation of the phosphate groups within the receptor binding site.

The sugar moiety of nucleosides and nucleotides in solution is known to exist in a rapid, dynamic equilibrium between extreme 2—exo/3'-endo (N—) and 2'-endo/3'-exo (S—) conformations as defined in the pseudorotational cycle. While the energy gap between N— and S-conformation is in the neighborhood of 4 kcal/mol, such a disparity can explain the difference between micromolar and nanomolar binding affinities. Using a molecular modeling approach, we have analyzed the sugar conformational requirements for a new class of bisphosphate ligands binding to the human $PSY_1$ receptor. As experimentally shown, the ribose ring Northern conformation appeared to be favored in recognition at human $PSY_1$ receptor (see Table 4). We have found new support to our recently presented hypothesis in which three important recognition regions are present in the bisphosphate molecular structures; The $N^1$ atom of the purine ring and the P atoms of both 3' and 5' phosphate groups. The N-conformation seems to be essential to maximize the electrostatic interactions between the negatively charged phosphates and the positively charged amino acids present in the receptor binding cleft, as well Arg128, Lys280, and Arg310.

Interestingly, the electrostatic contacts also appear to be crucial for the recognition of bisphosphate antagonists. Using superimposition analysis, a general pharmacophore model for the bisphosphate antagonists binding to the $PSY_1$ receptor has been proposed. According to the pharmacophore map, recognition of the bisphosphates antagonists at a common region inside the receptor binding site and, consequently, a common electrostatic potential profile is possible. As well for the agonists, the Northern conformation seems to be essential to maximize the electrostatic interactions between the negatively charged phosphates and the positively charged amino acids presents in the receptor binding cleft. As we predicted using the previously reported $PSY_1$ receptor model, sugar moiety does not seen to be crucial for the ligand recognition process.

As already described, the simple addition of the $N^6$-methyl group in several cases converted pure agonists to antagonists. From a pharmacological point of view, this is really a unique situation. With the addition of the $N^6$-methyl group it is not possible to have a double hydrogen-bonding interaction and, consequently, the activation pathway is blocked. However, for all the $N^6$-methyl antagonists the possibility to participate in at least one of the two possible hydrogen bonds appears to be very important for the increase in affinity at the $PSY_1$ receptor.

Chemical Synthesis

Nucleosides and synthetic reagents were purchased from Sigma Chemical Co. (St. Louis, Mo.) and Aldrich (St. Louis, Mo.). 6-Chloro-2'-deoxypurine riboside was obtained from Sigma. Several 2'-deoxynucleosides, including an anhydrohexitol-adenine nucleoside and 2'-deoxyaristeromycin were also synthesized.

Purity of compounds was checked using a Hewlett-Packard 1090 HPLC apparatus equipped with an SMT OD-5-60 RP-C18 analytical column (250×4.6 mm; Separation Methods Technologies, Inc., Newark, Del.) in two solvent systems. System A: Linear gradient solvent system: 0.1 M TEAA/$CH_3CN$ from 95/5 to 40/60 in 20 min and the flow rate was of 1 mL/min. System B: linear gradient solvent system: 5 mM TBAP/$CH_3CN$ from 80/20 to 40/60 in 20 min and the flow rate was of 1 mL/min. Peaks were detected by UV absorption using a diode array detector. All derivatives showed more than 95% purity in the HPLC systems.

Purification of most of the nucleotide analogues for biological testing was carried out on DEAE-A25 Sephadex columns as described above. However, compounds 7b and 8a-c required HPLC purification (system a, semi-preparative C18 column) of the reaction mixtures.

General Procedure of Phosphorylation.

Method A: The nucleoside (0.1 mmol) and Proton Sponge® (107 mg, 0.5 mmol) were dried for several h in high vacuum at room temperature and then suspended in 2 mL of trimethyl phosphate. Phosphorous oxychloride (Aldrich, 37 μL, 0.4 mmol) was added, and the mixture was stirred for 1 h at 0° C. The reaction was monitored by analytical HPLC (eluting with a gradient consisting of buffer: $CH_3CN$ in the ratio 95:5 to 40:60, in which the buffer was 0.1 M triethylammonium acetate (TEAA); elution time was 20 min; flow rate was 1 mL/min; column was SMT OD-5-60 RP-C18; detector was by UV in the $E_{max}$ range of 260-300 nm). The reaction was quenched by adding 2 mL of triethylammonium bicarbonate buffer and 3 mL of water. The mixture was subsequently frozen and lyophilized. Purification was performed on an ion-exchange column packed with Sephadex-DEAE A-25 resin, a linear gradient (0.01 to 0.5 M) of 0.5 M ammonium bicarbonate was applied as the mobile phase, and UV and HPLC were used to monitor the elution. All nucleotide bisphosphates were collected, frozen and lyophilized as the ammonium salts. All synthesized compounds gave correct molecular mass (high resolution FAB) and showed more than 95% purity (HPLC, retention times are reported in Table 4).

Method B: Nucleoside (0.1 mmol) dried for several h in high vacuum at room temperature was dissolved in 2 mL of dry THF. Lithium diisopropylamide solution (Aldrich, 2.0 M in THF, 0.4 mmol) was added slowly at −78° C. After 15 min tetrabenzyl pyrophosphate (Aldrich, 0.4 mmol) was added and the mixture was stirred for 30-60 min at −78° C. The reaction mixture was warmed to 0° C.-rt and stirred for an addition period ranging from 2 h to 24 h. Chromatographic purification (pTLC, $CHCl_3:CH_3OH(10:1)$ gave the tetrabenzyl phosphorylated compound. This compound (20 mg) was dissolved in a mixture of methanol (2 mL) and water (1 mL) and hydrogenated over a 10% Pd-on-C catalyst (10 mg) at rt for 62 h. The catalyst was removed by filtration and the methanol was evaporated. The residue was treated with ammonium bicarbonate solution and subsequently frozen and lyophilized. Purification, if necessary, was by the same procedure as in method A.

(N-Methanocarba-2'-deoxyadenosine-3',5'-bis(diammonium phosphate) (4a) [(IR,2S,4S,5S)-1-[(phosphato)methyl]-4-(6-aminopurin-9-yl)bicyclo[3.1.0.]-hexane-2-phosphate tetraammonium salt]

Starting from 16 mg (0.06 mmol) of (N)-methanocarba-2'deoxyadenosine and following the general phosphorylation procedure A we obtained 1.8 mg (0.0037 mmol, 5.5% yield) of the desired compound.

$^1$H-NMR ($D_2O$) ∂ 0.90 (1H, m, $CH_2$-6), 1.10 (1H, m $CH_2$6'), 1.82 (1H, m, CH-5), 1.91 (1H, m, $CH_2$-3') 2.23 (1H, m, $CH_2$-3'), 3.49 (1H, d, J=11.7 Hz, $CH_2$—OH), 4.16 (1H, d, J=6.9 Hz, $CH_2$-2'), 8.39 (1H, s, H-2), 8.54 (1H, s, H-8).

$^{31}$P-NMR ($D_2O$) ∂ 0.43 (s, 5'P); −0.19 (s, 3'P).

(N)-Methanocarba-$N^6$-methyl-2'deoxyadenosine-3', 5'-bis(diammonium phosphate) (4b)

(1R,2S,4S,5S)-1-[(phosphato)methyl]-4-(6-methylaminopurin-9-yl)bicyclo[[3.1.0.]-hexane-2-phosphate tetraammoniun salt]

13.5 mg (0.0170 mmol) of compound 18 was converted to the corresponding phosphoric acid analog using hydrogenation following the general procedure B. Purification was performed on an ion-exchange column packed with Sephadex-DEAF A-25 resin, linear gradient (0.01 to 0.5 M) of 0.5 M ammonium bicarbonate was applied as the elan to give 3.0 mg (0.0060 mmol, 35.3% yield) of the desired compound.

$^1$H-NMR ($D_2P$) ∂ 0.93-0.98 (1H, m, $CH_2$-6'), 1.17 (1H, m, $CH_2$-6'), 1.86-1.88 (1H, m, CH5'), 1.94-1.98 (1H, m, $CH_2$-3'), 2.23-2.31 (1H, m, $CH_2$-3'), 3.09 (3H, bs, $N^6$—$CH_3$), 3.61-3.64 (1H, m, $CH_2$OH), 4.51-4.55 (1H, m, $CH_2$OH), 5.01-5.03 (1H, m, CH-4'), 5.19-5.21 (1H, m, CH-2'), 8.22 (1H, s, H-2), 8.51 (1H, s, H-8). 31P-NMR ($D_2O$) ∂ 1.26, 1.92 (2s, 3'-P, 5'-P).

(N)-Methanocarba-$N^6$-methyl-2-chloro-2'-deoxyadenosine-3',5'-bis(diammonium phosphate) (4c)

[(1R,2S,4S,5S)-1[(phosphato)methyl]-4-(2-chloro-6-aminopurin-9-yl)bicyclo [3.1.0]-hexane-2-phosphate tetraammonium salt]

The nucleoside, compound 23, reacted with tetrabenzyl pyrophosphate, as in Method B, followed by an alternative deprotection procedure. Starting from 10 mg (0.0323 mmol) of (N)-methanorcarba-$N^6$-methyl-2-chloro-2'-deoxyadenosine and following the general phosphorylation procedure (Method B) we obtained 9.5 mg (0.0114 mmol, 35.3% yield) of the desired compound, (N)-methanocarba-$N^6$-methyl-2-chloro-2'-deoxyadenosine-3',5'-bis(dibenzyl phosphate).

$^1$H-NMR ($CDCl_3$)∂ 0.75-0.81 (H, m,$CH_2$-6'), 103-1.08 (1H, m, $CH_2$-6'), 1.49-1.51 (1H, m, CH-5'), 1.84-1.94 (1H, m, $CH_2$-3'), 1.99-2.10 (1H, m, $CH_2$-3'), 3.12 (3H, bs, $N^6$—$CH_3$), 4.11-4.20 (1H, m, $CH_2$OH), 4.50-4.55 (H, m, $CH_2$OH), 4.90-4.98, (8H, m, —$OCH_2$), 4.99-5.01 (1H, m, CH-4'), 5.23-5.30 (1H, m, CH-2'), 5.90 (1H, BS, NH), 7.20-7.29 (20H, m, $C_6H_5$), 7.82 (1H, s, H-8)

$^{31}$P-NMR ($D_2O$) ∂ −0.58 (s,5'P); −1.06 (s,3'P).

MS(Cl—$NH_3$) (M+1) 830 HRMS (FAB-) (M+Cs) Calcd. 962.1252; Found 962, 1252

9.5 mg (0.0114 mmol) of the tetrabenzyl-protected intermediate added to dry $CH_2Cl_2$ (1.0 mL) was cooled to −78° C. under argon and treated with 100 μL of boron trichloride solution (1M in $CH_2Cl_2$) and 100 μL of anisole. The reaction mixture was stirred for 12 hr at 0° C. to rt and extracted with triethylamine solution. Purification was performed on an ion-exchange column packed with Sephadex-DEAE A-25 resin, linear gradient (0.01 to 0.5 M) of 0.5 M ammonium bicarbonate was applied as the eluent to give 0.4 mg (0.0007 mmol, 6.52 yield) of the desired compound 4c.

$^1$H-NMR ($D_2O$) ∂0.91-0.96 (1H, m, $CH_2$-6'), 1.12-1.16 (1H, m, $CH_2$-6'), 1.80-1.84 (1H, m, CH-5'), 1.85-1.98 (1H, m, $CH_2$-3'), 2.20-2.50 (1H, m, $CH_2$-3'), 3.08 (3H, bs, $N^6$—$CH_3$), 3-57-3.60 (1H, m, $CH_2$OH), 4.52-4.67 (1H, m, $CH_2$OH), 4.94-4.96 (1H, m, CH-4'), 5.18-5.21 (1H, m, CH-2'), 8.52 (1H, s,H-8)

$^{31}$P-NMR ($D_2O$) ∂ 1.82, 2.52 (2s, 3'-P, 5'P)

(S)-Methanocarba-2', deoxyadeonosine-3',5'-bis(diammonium phosphate (5) [(1S,3S,4R,5S)-4-[(phosphato)methyl]-1-(6-aminopurin-9-yl)bicyclo[3.1.0]-hexane-3-phosphate tetraammonium salt]

Starting from 16 mg (0.06 mmol) of (S)-methanocarba-2'deoxyadenosine and following the general phosphorylation procedure A, we obtained 2.1 mg (0.0043 mmol, 7.55 yield) of the desired compound 5.

$^1$H-NMR ($D_2O$) ∂ 1.36 (1H, m, $CH_2$-6'), 1.53 (1H, t, J=4.8 Hz, $CH_2$-6'), 2.05 (1H, m, $CH_2$-5'), 2.30 (1H, m, CH-4'), 2.46 (2H, m, $CH_2$-2'), 3.97 (2H, m, $CH_2$OH), 4.45 (1H, d, J=6.6 Hz, CH-3'), 8.16 (1H, s, H-2), 8.30 (1H, s, H-8). $^{31}$P-NMR ($D_2O$) ∂ 0.85 (bs, 5'P); 0.31 (bs, 3'P).

[(1S,3S,4R,5S)-1-[(Hydroxy)methyl]-2-hydroxy-4-(6-methylaminopurin-9-1yl)bicyclo[3.1.0]-hexane (17b)

The Dimroth rearrangement (Scheme 2) was carried out on (N)-methanocarba-2'-deoxyadenosine. Specifically, the (N)-methanorcarba-2'-deoxyadenosine (17a, 50.0 mg, 0.191 mmol) was heated at 40° C. with methyl iodide (71.5 μL, 1.15 mmol) in dry DMF (2.0 mL) for 48 h. The solvent was evaporated under reduced pressure, and the residue was heated at 90° C. with ammonium hydroxide (4.0 mL) for 4 h. The water was evaporated, and the residue was purified by pTLC using MeOH; CHCl$_3$ (1:9) to afford compound 17b as a colorless solid (40 mg, 0.15 mmol, 76%).

$^1$H-NMR (CD$_3$OD) ∂ 0.77.-0.81 (1H, m, CH$_2$-6'), 1.03-1.07 (1H, m, CH$_2$-6'), 1.68-1.72 (1H, m, CH-5'), 1.79-1.89 (1H, m, CH$_2$-3'), 2.00-2.07 (1H, m, CH$_2$-3'), 3.12 (3H, bs, N$^6$—CH$_3$), 3-33 (1H, d, J=CH$_2$OH), 4.29 (1H, d, J=11.7 Hz, CH$_2$OH), 4.89-4.92 (1H, m, CH-4'), 5.02 (1H, d, J=6.9 Hz, CH-2'), 8.24 (1H, s, H-2), 8.49 (1H, s, H-8).

MS(CI—NH$_3$): 276 (M+1) 830 HRMS(FAB-) (M+Cs) Calcd. 275.1382; Found 275.1389.

(N)-Methanocarba-N$^6$-methyl-2'-deoxyadenosine-3',5'-bis(dibenzylphosphate) (18)

[(1S,2S,4S,5S)-1-[(dibenzylphosphato)methyl]-4-(6-methylaminopurin-9-yl)bicyclo[3.1.0]-hexane-2-dibenzylphosphate]

Starting from 20.0 mg (0.0726 mmol) of N-methanorcarba-N$^6$-methyl-2'-deoxyadenosine 17b and following the general phosphorylation procedure (Method B we obtained 13.5 mg (0.0170 mmol, 23.4% yield) of the desired protected intermediate, 18 as shown in Scheme 2.

$^1$H-NMR (CDCl$_3$) ∂ 0.73-0.78 (1H, m, CH$_2$-6'), 0.94-0.98 (1H, m, CH$_2$-6'), 1.53-1.54 (1H, m, CH-5'), 1.81-1.91 (1H, m, CH$_2$-3'), 2.05-2.13 (1H, m, CH$_2$-3'), 3.15 (3H, bs, N$^6$—CH$_3$), 3-70-3.83 (1H, m, CH$_2$OP), 4.49-4.55 (1H, m, CH$_2$OP), 4.89-5.00 (8H, m, OCH-$_2$), 5.02-5.06 (1H, m, CH-4'), 5.27-5.32 (1H, m, CH-2'), 5.86 (1H, bs, NH), 7.21-7.23 (20H, m, C$_6$H$_5$), 7.86 (1H, s,H-2), 8.31 (1H, s,H-8). $^{31}$P-NMR (D$_2$O) ∂ –0.56, –1.05 (2s, 3'-P, 5'P) HRMS (FAB-) (M-Cs) Calcd. 928.1641; Found 928.1700.

[(1S,2S,42,5S)-1-[(Benzyloxy)methyl]-2-benzyloxy-4-(2-6-dichloropurin-9-yl)bicyclo[3.1.0]-hexane (21)

To an ice cold solution of triphenylphosphine (278 mg, 1.06 mmol) in dry THF (2 mL) was added diethylazadicarboxylate (170, 1.06 mmol) dropwise under a nitrogen atmosphere, and the mixture was stirred for 20 min until the solution turned red orange (Scheme 3). This mixture was added dropwise to a cold stirred mixture of the starting alcohol (135 mg, 0.417 mmol) and 2.6-dichloropurine (157 mg, 0.883 mmol) under a nitrogen atmosphere. The reaction mixture was stirred in an ice bath for 30 min and then allowed to warm to room temperature, and stirring continued for 12 h. Solvent was removed by nitrogen purge, and the residue was purified by pTLC using EtOAc petroleum ether (1:1) to afford a thick liquid (132 mg, 0.263 mmol, 64%).

$^1$H NMR: (CD$_3$OD) δ 0.85 (m, 1H), 1.13 (m, 1H), 1.59 (m, 1H), 1.68 (m, 1H), 2.06 (m, 1H), 3.17 (d, J=10.8 Hz, 1H), 4.11-4.57 (m, 5H), 5.20 (d, J=6.9 Hz, 1H), 6.6 (bs, 1H), 7.23-7.37 (m, 10H), 8.98 (s, 1H).

MS: (EI) 494 (M+).

[(1R,2S,4S,5S)-1-[(Benzyloxy)methyl]-2-benzyloxy-4-(2-chloro-6-methylaminopurin-9-yl)bicyclo[3.1.0]-hexane (22)

Compound 21 (100 mg, 0.202 mmol) was dissolved in methylamine in methanol (30% solution, 3 mL) and was stirred at rt for 12 h under a nitrogen atmosphere. The solvent was evaporated, and the crude product was purified by pTLC using EtOAc:petroleum ether (6:4) to afford 22 as a light yellow solid (86 mg, 0.176 mmol, 88%).

$^1$H NMR: (CD$_3$OD) δ 0.70 (m, 1H), 1.06 (m, 1H), 1.50 (m, 1H), 1.76 (m, 1H), 1.96 (m, 1H), 3.01 (s, 3H), 3.08 (m, 2H), 4.03 (m, 4H), 4.45 (bs, 1H), 5.02 (bs, 1H), 8.38 (s, 1H).

MS: (Cl): 490 (M+1).

[(1R,2S,42,5S)-1-[(Hydroxy)methyl]-2-hydroxy-4-(2-chloro-6-methylaminopurin-9-yl)bicyclo[3.1.0]-hexane (23)

Compound 22 (40 mg 0.0816 mmol) was dissolved in dry CH$_2$Cl$_2$ (1.0 mL), and hydrogenated using BCl$_3$ (1M in CH$_2$Cl$_2$, 175 μL) for 50 min at −78° C. under argon. The solvent was evaporated, and the crude product was purified by pTLC using CHCl$_3$: MeOH (10:1) to afford 23 as a light yellow solid (10.0 mg, 0.0323 mmol, 39.6%).

$^1$H NMR: (CD$_3$OD) ∂ 0.77-0.81 (1H, m, CH$_2$-6'), 1.02-1.05 (1H, m, CH$_2$-6'), 1.65-1.68 (1H, m, CH-5'), 1.78-1.91 (1H, m, CH$_2$-3'), 1.99-2.07 (1H, m, CH$_2$-3'), 3.08 (3H, bs, N$^6$—CH$_3$), 3.37 (1H, d, J=11.7 Hz, CH$_2$OH), 4.27 (1H, d, J=11.7 Hz, CH$_2$OH), 4.89-4.91 (1H, m, CH-4), 4.97 (1H, d, J=6.8 Hz, CH-2'), 8.46 (1H, s, H-8).

MS: (CI—NH$_3$): 310 (M+1), HRMS (FAB-): Calcd 309.0992, Found 309.0991.

Pharmacological Analyses.

P2Y$_1$ receptor promoted stimulation of inositol phosphate formation by adenine nucleotide analogues was measured in turkey erythrocyte membranes as previously described. The K$_{0.5}$ values were averaged from 3-8 independently determined concentration-effect curves for each compound. Briefly, 1 mL of washed turkey erythrocytes was incubated in inositol-free medium (DMEM; Gibco, Gaithersburg Md.) with 0.5 mCi of 2-[$^3$H]myo-inositol (20Ci/mmol: American Radiolabelled Chemicals, Inc., St. Louis Mo.) for 18-24 h in a humidified atmosphere of 95% air/5% CO$_2$ at 37° C. Erythrocyte ghosts were prepared by rapid lysis in hypotonic buffer (5 mM sodium phosphate, pH 7.4, 5 mM MgCl$_2$, 1 mM EGTA) as described. Phospholipase C activity was measured in 25 μL of [$^3$H]inositol-labeled ghosts (approximately 175 μg of protein, 200-500,000 cpm/assay) in a medium containing 424 μM CaCl$_2$, 0.91 mM MgSO$_4$, 2 mM EGTA, 115 mM KCl, 5 mM KH$_2$PO$_4$, and 10 mM Hepes pH 7.0. Assays (200 μL final volume) contained 1 μM GTPγS and the indicated concentrations of nucleotide analogues. Ghosts were incubated at 30° C. for 5 min, and total [$^3$H]inositol phosphates were quantitated by anion exchange chromatography as previously described.[7,36]

Data Analysis.

Agonist potencies were calculated using a four-parameter logistic equation and the GraphPad software package (GraphPad, San Diego, Calif.). EC$_{50}$ values (mean±standard error) represent the concentration at which 50% of the maximal effect is achieved. Relative efficacy (%) was determined by comparison with the effect produced by a maximal effective concentration of 2-MeSADP in the same experiment.

Antagonist $IC_{50}$ values (mean±standard error) represent the concentration needed to inhibit by 50% the effect elicited by 10 nM 2-MeSADP. The percent of maximal inhibition is equal to 100 minus the residual fraction of stimulation at the highest antagonist concentration.

All concentration-effect curves were repeated in at least three separate experiments carried out with different membrane preparations using duplicate or triplicate assays.

TABLE 3

Stimulation of PLC at turkey erythrocyte $P2Y_1$ receptors (agonist effect) and the inhibition of PLC stimulation elicited by 10 nM 2-MeSADP (antagonist effect), for at least two separate determinations.

| Compound | Agonist Effect, % of maximal increase[a] | $EC_{50}$, μM[a] | Antagonist Effect, % of maximal inhibition[b] | $IC_{50}$, μM[b] (n) |
|---|---|---|---|---|
| 1a[c,e] (MRS 2179) | NE | | 99 ± 1 | 0.331 ± 0.059 (5) |
| 1b[e] | NE | | 95 ± 1 | 0.206 ± 0.053 |
| 1c[e] | 4 | d | 96 ± 2 | 1.85 ± 0.74 |
| 1d[e] | 6 ± 2 | d | 94 ± 2 | 0.362 ± 0.119 |
| 4a | 92 ± 5 | 0.155 ± 0.021 | NE | |
| 4b | NE | | 100 | 0.157 ± 0.060 |
| 4c | NE | | 100 | 0.0516 ± 0.0008 |
| 5 | 41 ± 13 | 13.3 | 34% at 100 μM | small decrease |

[a]Agonist potencies were calculated using a four-parameter logistic equation and the GraphPad software package (GraphPad, San Diego, CA). $EC_{50}$ values (mean ± standard error) represent the concentration at which 50% of the maximal effect is achieved. Relative efficacies (%) were determined by comparison with the effect produced by a maximal effective concentration of 2-MeSADP in the same experiment. Small increase refers to ≦10% at 100 μM.
[b]Antagonist $IC_{50}$ values (mean ± standard error) represent the concentration needed to inhibit by 50% the effect elicited by 10 nM 2-MeSADP. The percent of maximal inhibition is equal to 100 minus the residual fraction of stimulation at the highest antagonist concentration.
[c]1a, MRS 2179; 4c, MRS 2279.
d $EC_{50}$ was not calculated for increases of ≦10% at 100 μM.
[e]values from refs. 17, 19.
NE no effect at 100 μM.

Abbreviations

AIBN, 2,2'-azobisisobutyronitrile;
ATP, adenosine 5'-triphosphate;
DBU, 1,8-diazabicyclo[5.4.0]undec-7-ene;
DCTIDS, 1,3-dichlorotetraisopropyl-1,1,3,3,-disiloxane;
DEAD, diethylazadicarboxylate;
DEAE, diethylaminoethyl;
DMAP, 4-dimethylaminopyridine;
DMF, dimethylformamide;
DMSO, dimethylsulfoxide;
FAB, fast atom bombardment (mass spectroscopy);
HPLC, high pressure liquid chromatography;
MS, mass spectroscopy;
HRMS, high resolution mass spectroscopy;
LDA, lithium diisoproylamide;
2-MeSADP, 2-methylthioadenosine-5'-diphosphate;
TBAP, tetrabutylammonium phosphate;
TEAA, triethylammoniun acetate;
THF, tetrahydrofuran;

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

TABLE 4

Synthetic data for nucleotide derivatives, including structural verification using high resolution mass spectroscopy and purity verification using HPLC.

| No | Formula | FAB (M − H⁺) Calcd | FAB (M − H⁺) Found | HPLC (rt; min)[a] System A | HPLC (rt; min)[a] System B | Method, Yield (%)[b] |
|---|---|---|---|---|---|---|
| 2 | $C_{10}H_{15}O_9N_5P_2$ | 410.0267 | 410.0269 | 3.53 | 10.72 | B, 21.7 |
| 3b | $C_{12}H_{19}O_8N_5P_2$ | 422.0631 | 422.0664 | 3.41 | 8.21 | B, 8.0 |
| 4a | $C_{12}H_{17}O_8N_5P_2$ | 420.0474 | 420.0482 | 3.92 | 7.30 | A, 5.5 |
| 4b | $C_{13}H_{19}O_8N_5P_2$ | 434.0631 | 434.0622 | 5.91 | 7.83 | B, 8.3 |
| 4c | $C_{13}H_{18}O_8N_5P_2Cl$ | 468.0241 | 468.0239 | 8.05 | 8.54 | B, 2.3 |
| 5 | $C_{12}H_{17}O_8N_5P_2$ | 420.0474 | 420.0481 | 4.02 | 6.84 | A, 7.5 |
| 6 | $C_{11}H_{16}O_8N_5P_2Cl$ | 442.0084 | 442.0070 | 6.67 | 6.82 | A, 24.3 |
| 7b | $C_{12}H_{20}O_{12}N_5P_3$ | 518.0237 | 518.0243 | 4.98 | 12.74 | A, 1.8 |
| 7c | $C_{12}H_{19}O_9N_5P_2$ | 438.0580 | 438.0580 | 4.63 | 9.36 | B, 50.1 |
| 7d | $C_{12}H_{18}O_9N_5P_2Cl$ | 472.0201 | 472.0190 | 5.67 | 9.97 | B, 31.3 |
| 8a | $C_{12}H_{20}O_8N_6P_2$ | 437.0740 | 437.0721 | 2.37 | 8.78 | 8.0 |
| 8b | $C_{12}H_{21}O_{11}N_6P_3$ | 517.0403 | 517.0404 | 2.,42 | 9.23 | 7.2 |
| 8c | $C_{12}H_{22}O_{14}N_6P_4$ | 597.0066 | 597.0053 | 2.96 | 10.02 | 4.0 |

[a]Purity of each derivative was ≧95%, as determined using HPLC with two different mobile phases. System A: gradient of 0.1M $TEAA/CH_3CN$ from 95/5 to 40/60 and System B: gradient of 5 mM $TBAP/CH_3CN$ from 80/20 to 40/60.
[b]Phosphorylation methods: Method A refers to use of phosphorous oxychloride, and Method B refers to use of tetrabenzyl pyrophosphate/lithium diisopropylamide followed by hydrogenation. The percent yields refer to overall yield for each phosphorylation sequence. For the method of synthesis of 8 refer to Experimental Section.

What is claimed is:

1. A compound of the formula:

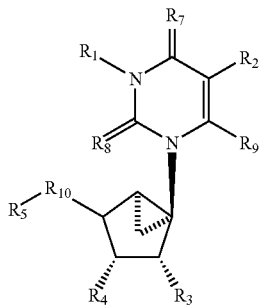

wherein $R_1$ is hydrogen, alkenyl, alkynyl, or aminoalkyl;
$R_2$ and $R_9$ are independently hydrogen, alkyl, alkenyl, alkynyl, or aminoalkyl;
$R_3$, $R_4$, and $R_5$, are each independently hydrogen, hydroxyl, alkoxy, alkyl, alkenyl, alkynyl, aryl, acyl, alkylamino, arylamino, phosphoryl, or phosphonyl;
$R_8$ and $R_7$ are each independently sulfur or oxygen;
and $R_{10}$ is methylene, dihalomethyl, carbonyl, or sulfoxide;
or a salt of said compound;
with the proviso that when $R_1$ is hydrogen, $R_2$ is methyl, $R_4$ and $R_5$ are hydroxyl, $R_7$ and $R_8$ are O, $R_9$ is hydrogen, and $R_{10}$ is methylene, $R_3$ is not hydrogen.

2. A pharmaceutical composition comprising a pharmaceutically acceptable carrier and a compound or salt of claim 1.

3. The compound or salt of claim 1, wherein the phosphoryl group is a diphosphoryl group.

4. The compound or salt of claim 3, wherein $R_1$, $R_2$, and $R_9$ are hydrogen, $R_7$ and $R_8$ are oxygen, $R_{10}$ is methylene, $R_5$ is diphosphoryl, and $R_3$ and $R_4$ are hydrogen or hydroxyl.

5. The compound or salt of claim 4, wherein $R_3$ and $R_4$ are hydroxyl.

6. The compound or salt of claim 4, wherein $R_3$ is hydrogen and $R_4$ is hydroxyl.

7. A pharmaceutical composition comprising a pharmaceutically acceptable carrier and a compound or salt of claim 3.

8. A pharmaceutical composition comprising a pharmaceutically acceptable carrier and a compound or salt of claim 4.

9. A pharmaceutical composition comprising a pharmaceutically acceptable carrier and a compound or salt of claim 5.

10. A pharmaceutical composition comprising a pharmaceutically acceptable carrier and a compound or salt of claim 6.

11. A method of treating a mammal for epilepsy comprising administering to the mammal an effective amount of a compound or salt of claim 1.

12. A method of treating a mammal for epilepsy comprising administering to the mammal an effective amount of a compound or salt of claim 3.

13. A method of treating a mammal for epilepsy comprising administering to the mammal an effective amount of a compound or salt of claim 4.

14. A method of treating a mammal for epilepsy comprising administering to the mammal an effective amount of a compound or salt of claim 5.

15. A method of treating a mammal for epilepsy comprising administering to the mammal an effective amount of a compound or salt of claim 6.

16. A method of treating a mammal for Parkinson's disease comprising administering to the mammal an effective amount of a compound or salt of claim 1.

17. A method of treating a mammal for Huntington's disease comprising administering to the mammal an effective amount of a compound or salt of claim 1.

* * * * *